(12) United States Patent
Satoh et al.

(10) Patent No.: US 6,515,747 B1
(45) Date of Patent: Feb. 4, 2003

(54) METHOD AND DEVICE FOR MEASURING A SUBSTANCE CONCENTRATION IN A LIQUID

(75) Inventors: Osamu Satoh, Sagamihara (JP); Tsutomu Sasaki, Yokohama (JP); Masahiko Itaya, Akishima (JP)

(73) Assignee: Ricoh Company, Ltd., Tokyo (JP)

( * ) Notice: Subject to any disclaimer, the term of this patent is extended or adjusted under 35 U.S.C. 154(b) by 0 days.

(21) Appl. No.: 09/517,082

(22) Filed: Mar. 1, 2000

(30) Foreign Application Priority Data

Mar. 1, 1999 (JP) .......................... 11-052948

(51) Int. Cl.[7] ............................................. G01N 21/59
(52) U.S. Cl. .......................... 356/436; 356/440; 399/64
(58) Field of Search ................... 356/436, 440, 356/441, 442; 399/30, 64

(56) References Cited

U.S. PATENT DOCUMENTS

| | | | |
|---|---|---|---|
| 4,204,766 A | * 5/1980 | Harada | 399/57 |
| 4,640,605 A | 2/1987 | Ariyama et al. | |
| 4,720,731 A | 1/1988 | Suzuki et al. | |
| 4,800,839 A | 1/1989 | Ariyama et al. | |
| 4,801,965 A | 1/1989 | Mochizuki et al. | |
| 4,833,500 A | 5/1989 | Mochizuki et al. | |
| 5,021,834 A | 6/1991 | Tsuruoka et al. | |
| 5,155,534 A | 10/1992 | Kurotori et al. | |
| 5,156,308 A | 10/1992 | Aoyama | |
| 5,248,847 A | 9/1993 | Aoyama | |
| RE34,437 E | 11/1993 | Ariyama et al. | |
| 5,602,647 A | * 2/1997 | Xu et al. | 356/440 |
| 5,642,188 A | 6/1997 | Mochizuki et al. | |
| 5,652,080 A | 7/1997 | Yoshino et al. | |
| 5,666,616 A | 9/1997 | Yoshino et al. | |
| 5,678,126 A | 10/1997 | Rathbun | |
| 5,708,938 A | 1/1998 | Takeuchi et al. | |
| 5,897,240 A | * 4/1999 | Yoo | 399/30 |
| 5,923,930 A | 7/1999 | Tsukamoto et al. | |
| 5,937,247 A | 8/1999 | Takeuchi et al. | |
| 5,960,231 A | * 9/1999 | Martinez | 399/30 |
| 5,987,281 A | 11/1999 | Kurotori et al. | |
| 5,987,282 A | 11/1999 | Tsukamoto et al. | |
| 5,999,779 A | 12/1999 | Takeuchi | |
| 6,061,540 A | 5/2000 | Takeda | |
| 6,115,576 A | 9/2000 | Nakano et al. | |
| 6,131,001 A | 10/2000 | Tsukamoto et al. | |
| 6,134,394 A | 10/2000 | Tsukamoto et al. | |
| 6,148,169 A | 11/2000 | Tsukamoto | |
| 6,154,624 A | 11/2000 | Sasaki et al. | |
| 6,236,825 B1 | 5/2001 | Takeuchi | |

FOREIGN PATENT DOCUMENTS

JP          10-104955          4/1998

* cited by examiner

Primary Examiner—Richard A. Rosenberger
(74) Attorney, Agent, or Firm—Oblon, Spivak, McClelland, Maier & Neustadt, P.C.

(57) ABSTRACT

A method and apparatus for measuring a substance concentration in a liquid wherein a continuously variable thickness of the liquid is formed, and light is emitted such that a portion of the light passes through the formed continuously variable thickness of the liquid, an electrical signal is generated according to the portion of the light that passes through the formed continuously variable thickness of the liquid, and the substance concentration in the liquid is determined based on the generated electrical signal.

42 Claims, 17 Drawing Sheets

| AG | SUBSTANCE CONCENTRATION IN A LIQUID |
|---|---|
| AG1 | C1% |
| AG2 | C2% |
| AG3 | C3% |
| AG4 | C4% |
| ⋮ | ⋮ |
| AGN-1 | CN-1% |
| AGN | CN% |

METHOD AND DEVICE FOR MEASURING A SUBSTANCE CONCENTRATION IN A LIQUID

CROSS-REFERENCE TO RELATED APPLICATIONS

This application claims priority under 35 U.S.C. 119 to Japanese Patent Application No. 11-052948 filed on Mar. 1, 1999, the entire contents of which are incorporated herein by reference.

BACKGROUND OF THE INVENTION

1. Field of the Invention

The present invention relates to a method and a device for measuring a substance concentration in a liquid. More particularly, the present invention relates to a method and a device for optically measuring a substance concentration in a liquid.

2. Discussion of the Background

A liquid containing one or more substances that are completely dissolved is called a solution. The liquid that dissolves the substances in the solution is called a solvent, and a substance dissolved in the solution is called a solute. A liquid containing one or more substances that are dispersed (i.e. not completely dissolved) is called a dispersing liquid or a dispersion. The liquid in a dispersion is called a dispersion medium or a dispersing liquid, and a substance dispersed in the dispersing liquid is called a dispersoid.

Measurements of concentration of a substance such as a solute or a dispersoid, in a liquid such as a solution or a dispersing liquid, are performed in various fields. As an example, an image forming apparatus such as a laser printer, a photocopier, a facsimile machine, etc., uses a liquid developer which is a solution or a dispersing liquid. The liquid developer includes a toner as a solute and/or a dispersoid, and a carrier liquid as a solvent and/or a dispersion medium. The toner in the liquid developer is electrically charged and therefore adheres to an electrostatic latent image on an image bearer, such as a photoconductor drum. Thus, the electrostatic latent image is developed to a toner image.

In an image forming operation, measuring the toner concentration in the liquid developer and keeping the toner concentration within a certain range according to the measurement is important for forming quality images. Otherwise, a formed image may be degenerated, having, for example, background soiling, a low image density, etc. For measuring the toner concentration in the liquid developer, a sensor having a light-emitting device and a light-receiving device is known.

In a first such sensor, the light-emitting device and the light-receiving device are disposed facing each other and separated by a predetermined distance. The light-emitting device emits light toward the light-receiving device through the liquid developer, and the light-receiving device receives the emitted light. A part of the emitted light is absorbed by the liquid developer. Therefore the intensity of the received light is decreased in comparison with that of the emitted light. As the toner concentration increases, the received light decreases, and as toner concentration decreases, the received light increases. Thus, the toner concentration in the liquid developer is measured based on the intensity of light received by the light-receiving device.

In a second such sensor, both the light-emitting device and the light-receiving device are disposed to face a light reflecting body to which a liquid developer has been applied. The toner concentration is also measured based on the intensity of light received by the light-receiving device. As the light reflecting body, for example, a photoconductive drum, an intermediate transfer belt, a developing belt, etc., may be used.

Generally, a carrier liquid, such as a solvent and/or a dispersion medium, is relatively transparent and a toner is relatively opaque or a light absorbing substance. Therefore the optical transmittance of the liquid developer varies depending upon the toner concentration in the liquid developer. Accordingly, in both types of the above-described sensors, toner concentration may be accurately measured using the output of those light-receiving devices over a certain range. However, as recognized by the present inventors, the measurement of a relatively wide range of toner concentrations causes some difficulties, such as a lack of linearity between the output of the sensor and the toner concentration.

FIG. 1 is a graph illustrating a relationship between a toner concentration in a liquid developer and an output voltage of the second above-noted sensor. For generating the data in the graph, a 50 micrometer thick layer of liquid developer was applied to a light reflecting body opposite the light-emitting device and the light-receiving device. As illustrated, at relatively low and high toner concentrations, the gradients of tangents to the curve become smaller in comparison to the middle range toner concentration. In other words, the sensitivity of the toner concentration sensor becomes smaller at relatively low and relatively high toner concentrations. In addition, at a low toner concentration, the output voltage approaches the saturated output voltage Vm of the sensor, and at a high toner concentration, the output voltage approaches zero volts.

FIG. 2 is a graph illustrating a relationship between the thickness of a liquid developer on the light reflecting body and the output voltage of the second above-noted sensor at different toner concentrations of 10, 15, 10 and 25% in the liquid developer. Referring to FIG. 2, the output voltage of the sensor approximately decreases with increasing thickness of the developer. At a relatively thin developer thicknesses, the output voltage becomes close to a saturated voltage Vm, and at relatively thick developer thicknesses, the output voltage becomes close to zero volts for any concentration of the developer.

As another example, U.S. Pat. No. 5,678,126 describes a toner concentration sensor and a method utilizing a light source, a light splitter, and two light detectors.

SUMMARY OF THE INVENTION

The present invention has been made in view of the above-discussed and other problems and to overcome the above-discussed and other problems associated with the background methods and apparatus.

Accordingly, one object of the present invention is to provide a novel method and device for measuring a substance concentration in a liquid in a relatively simple manner and that can measure a relatively wide range of substance concentrations in a liquid.

These and other objects are achieved according to the present invention by providing a novel method and device for measuring a substance concentration in a liquid wherein a continuously variable thickness of the liquid is formed, and light is emitted such that a portion of the light passes through the formed continuously variable thickness of the liquid, an electrical signal is generated according to the portion of the light that has passed through the formed continuously variable thickness of the liquid, and the substance concentration in the liquid is determined based on the generated electrical signal.

BRIEF DESCRIPTION OF THE DRAWINGS

A more complete appreciation of the present invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
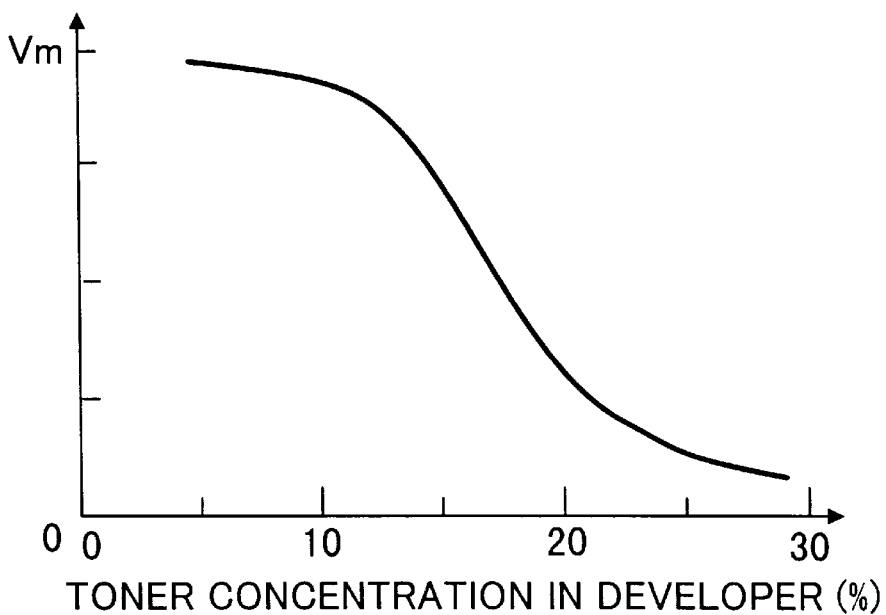
FIG. 1 is a graph illustrating a relationship between a toner concentration in a liquid developer and an output voltage of a conventional toner concentration sensor.
Figure 2:
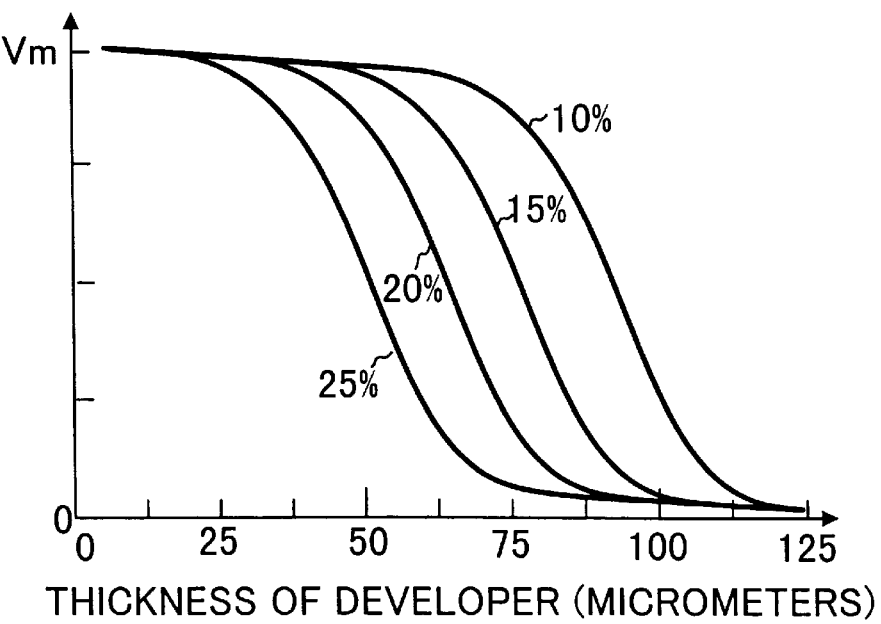
FIG. 2 is a graph illustrating a relationship between a thickness of the liquid developer and an output voltage of the conventional toner concentration sensor at different toner concentrations in the liquid developer.
Figure 3:
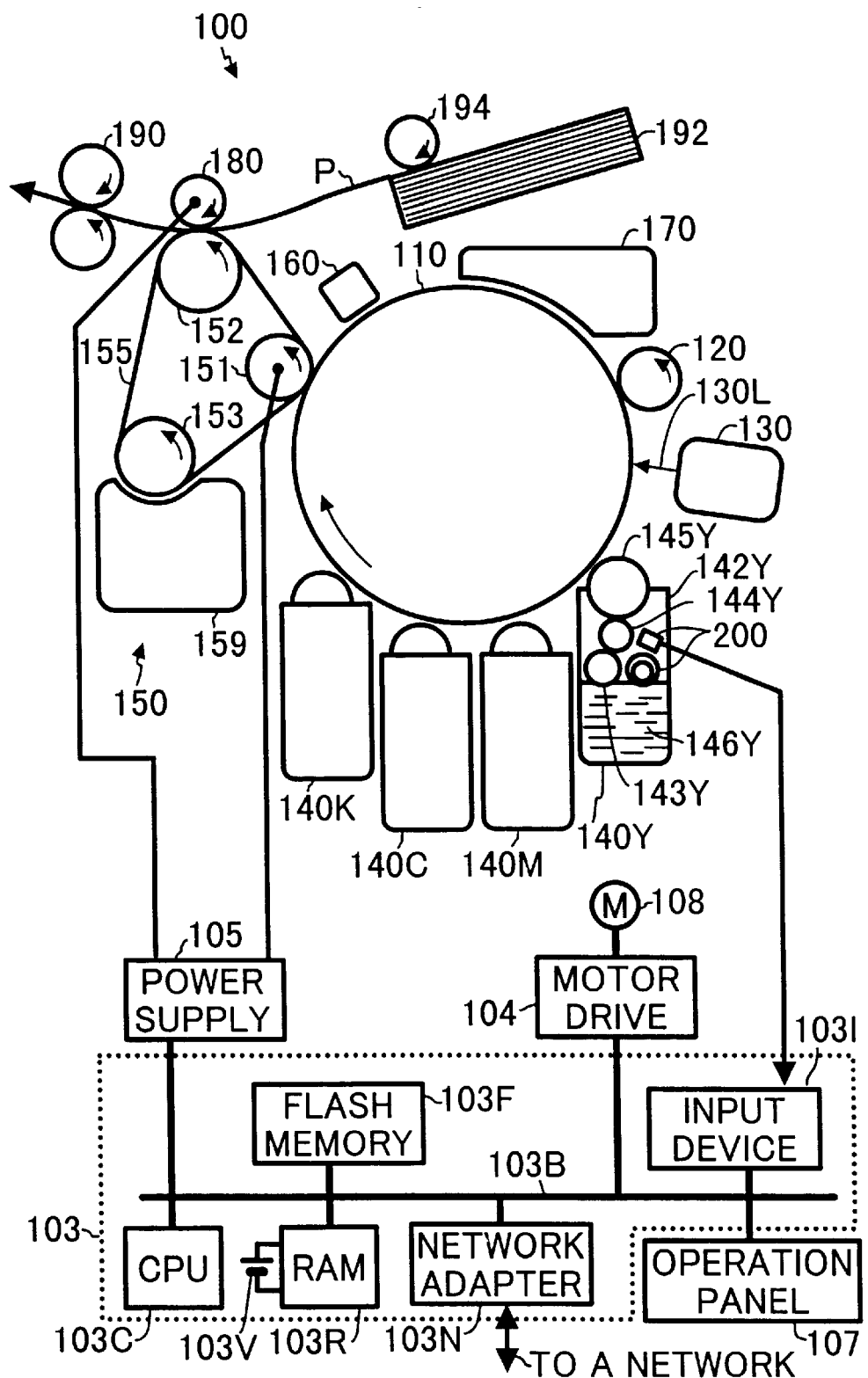
FIG. 3 is a schematic diagram illustrating a laser printer provided with a concentration measuring device configured according to one example of the present invention.

Referring now to the drawings, wherein like reference numerals designate identical or corresponding parts throughout the several views, and more particularly to FIG. 3 which provides a schematic view illustrating a laser printer 100 provided with an example of a concentration measuring device 200 configured according to the present invention. The laser printer 100 includes a photoconductive drum 110 as an image bearer surrounded by a electrical charging roller 120, a raster scanning module 130, liquid developing devices 140K, 140C, 140M and 140Y, an intermediate transfer device 150, a discharging device 160, a cleaning device 170. The laser printer 100 also includes a transfer roller 180, a fixing device 190, a paper tray 192, and a paper feed roller 194. The laser printer 100 further includes a control module 103, a motor drive 104, a power supply 105, a control panel 107, and a motor 108.

The control module 103 includes an address and data bus 103B, a network adaptor 103N, a central processing unit (CPU) 103C, a random accesses memory (RAM) 103R, a flash memory 103F, and an input device 103I. The flash memory 103F stores instruction codes executed by the CPU 103C. The flash memory 103F may be replaced with other types of data storing devices, such as a read-only memory, a hard disk, a CD-ROM, a DVD-ROM, etc. The RAM 103R may have a backup battery 103V. The input device 103I includes digital input terminals, analog input terminals, and an analog to digital converter. Therefore, an analog input signal is converted into digital data, and then the converted data is sent to another device such as, the CPU 103C, the RAM 103R, etc., via the address and data bus 103B.

The intermediate transfer device 150 includes a counter-clockwise rotating intermediate transfer belt 155, spanned by rollers 151, 152 and 153, and a belt cleaning device 159 provided with a cleaning blade. The roller 151 also functions as an electrode for biasing a portion where the transfer belt 155 contacts the photoconductive drum 110 at an appropriate voltage supplied by the power supply 105. The transfer roller 180 contacts the intermediate transfer belt 155 at a position opposite the roller. The power supply 105 also supplies an appropriate transfer voltage to the transfer roller 180.

The liquid developing devices 140K, 140C, 140M, and 140Y contain a black developer, a cyan developer, a magenta developer, and a yellow developer, respectively, and liquid developing devices 140K, 140C, 140M, and 140Y may be structured by substantially identical functional elements except for the color developers. As an example, the liquid developing device 140Y includes a tank 142Y, a supply roller 143Y, a coating roller 144Y, and a developing roller 145Y. The tank 142Y contains the yellow developer 146Y, and the concentration measuring device 200 is disposed such that a lower portion of device 200 is dipped in the yellow developer 146Y.

The supply roller 143Y is also disposed such that a lower portion of it is dipped in the yellow developer 146Y, and supplies the yellow developer 146Y to the coating roller 144Y. The coating roller 144Y forms a thin liquid layer of the developer 146Y on the coating roller 144Y being supplied by the supply roller 143Y, and coats the developing roller 145Y with using the formed thin developer layer. The developing roller 145Y coated with the liquid developer contacts the photoconductive drum 110, and thereby an electrostatic latent image carried on the photoconductive drum 110 is developed by the yellow developer 146Y, i.e., a yellow toner image is formed on the photoconductive drum 110.

Each of the liquid developing devices 140K, 140C, and 140M respectively develops an electrostatic latent image carried on the photoconductive drum 110 by the black developer, cyan developer, and magenta developer, in substantially the same manner as the yellow liquid developing device 140Y operates.

An image forming operation is performed as follows. The control module 103 receives a print command accompanying print data from an external apparatus, such as a personal computer via a network and the network adaptor 103N. Then, the control module 103 activates the motor drive 104 to rotate the motor 108. The motor 108 rotates the photoconductive drum 110 and other devices counterclockwise. Then, the electrical charging roller 120 charges the surface of the photoconductive drum 110 at a substantially uniform voltage. The charged photoconductive drum 110 is then exposed by a raster scanning laser beam (130L in FIG. 3) generated by the raster scanning module 130 according to the received print data. Thus, an electrostatic latent image according to the received print data is formed on the photoconductive drum 110.

One of the liquid developing devices 140K, 140C, 140M and 140Y is activated to develop the electrostatic latent image carried on the photoconductive drum 110, and thereby one of the four color toner images is formed on the photoconductive drum 110. The toner image is then conveyed to a position opposing the roller 151. There, the toner image is transferred from the photoconductive drum 110 to the intermediate transfer belt 155 by an electric field generated by a bias voltage supplied by the power supply 105.

The photoconductive drum 110 is then conveyed to a position opposing the discharging device 60 where electrical charge on the photoconductive drum 110 is discharged. The toner particles that remain on the photoconductive drum 110, i.e., toner particles which have not been transferred to the transfer belt 155, are removed by the cleaning device 170.

By repeating the above-described operation four times with the black developer, the cyan developer, the magenta developer, and the yellow developer, respectively, a set of superimposed four color toner images or a full color toner image is formed on the intermediate transfer belt 155. When the superimposed four color toner images on the intermediate transfer belt 155 arrive at a position that opposes the transfer roller 180, a sheet of paper P is also conveyed by the paper feed roller 194 from the paper tray 192. While the sheet P is conveyed at substantially the same speed as the circumferential speed of the intermediate transfer belt 155, the power supply 105 supplies the transfer roller 180 with an appropriate voltage, with the polarity of the voltage opposite to the polarity of the electrically charged toner particles. Thus, the toner image on the intermediate transfer belt 155 is attracted toward the sheet P and transferred to the sheet P. The toner particles that remain on the intermediate transfer belt 155, i.e., toner particles which have not been transferred to the sheet P, are removed by the belt cleaning device 159.

The sheet P having the transferred toner image is further conveyed to the fixing device 190 where the toner image is fixed on the sheet P, and then the fixed sheet P is discharged from the laser printer 100 as a printed sheet.

Figure 4:
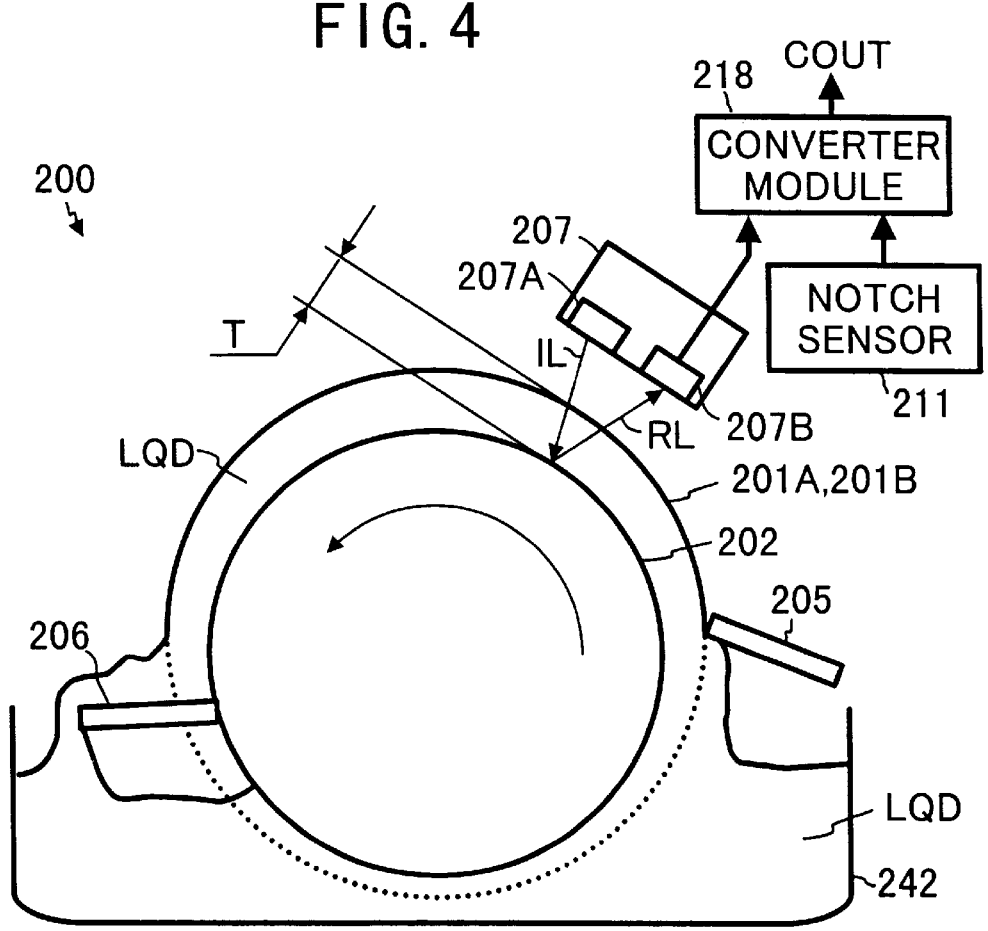
FIG. 4 is a schematic sectional view illustrating an example of a concentration measuring device configured according to the present invention.
Figure 5:
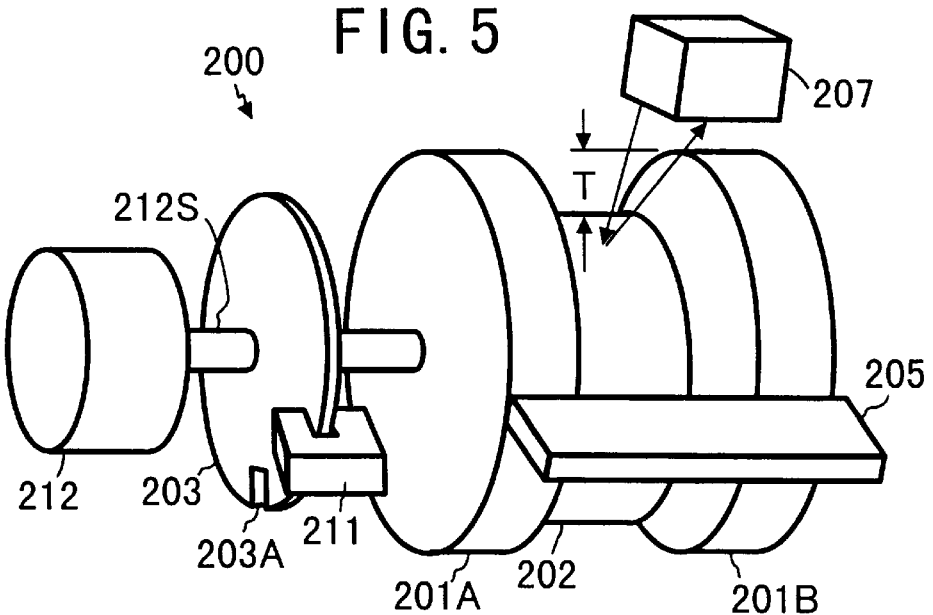
FIG. 5 is a schematic perspective view of the concentration measuring device of FIG. 4.

FIG. 4 is a schematic sectional view illustrating a structure of a concentration measuring device 200 as an example configured according to the present invention, and FIG. 5 is a schematic perspective view of the concentration measuring device 200 of FIG. 4. Referring to FIG. 4, the concentration measuring device 200 includes large disks 201A and 201B, a small disk 202, a first doctor blade 205, a second doctor blade 206, an optical sensor 207, a notch sensor 211, and a converter module 218.

The optical sensor 207 includes a light emitting device 207A and a light receiving device 207B both opposite the outer surface of the small disk 202. The circumference of the small disk 202 reflects light. Therefore, when the light emitting device 207A emits light (denoted as IL) and irradiates the circumference of the small disk 202, the light receiving device 207B can receive reflected light (denoted as RL). For effectively reflecting light, the circumference of the small disk 202 may be polished like a mirror. The first doctor blade 205 contacts the outer surfaces of the large disks 201A and 201B, and the second doctor blade 206 contacts the outer surface of the small disk 202. A tank 242 contains a liquid LQD, which is a solution or a dispersing liquid i.e., the liquid LQD includes a substance such as, a solute or a dispersoid, the concentration of which is measured. Lower portions of the large disks 201A and 201B, and the small disk 202 are disposed in the liquid LQD.

The converter module 218 receives inputs from the light receiving device 207B and the notch sensor 211, and converts the output voltage of the light receiving device 207B into a substance concentration signal or data from the liquid LQD, denoted as COUT.

Referring to FIG. 5, the concentration measuring device 200 further includes a notched disk 203 and a motor 212. The large disks 201A and 201B, the small disk 202 and the notched disk 203 are tightly mounted on a shaft 212S of the motor 212, so that those disks are rotated as a single body by the motor 212. The notch sensor 211 detects a notch 203A, which is provided in the notched disk 203. Accordingly, the angular position of the large disks 201A and 201B and the small disk 202 can be determined as a product of the angular velocity and the time from the time when the notch sensor 211 detects a notch 203A.

The large disks 201A and 201B have substantially identical external diameters and are concentrically mounted on the shaft 212S of the motor 212. The small disk 202 has a smaller external diameter than the diameter of large disks 201A and 201B. The small disk 202 is sandwiched by the large disks 201A and 201B and eccentrically mounted on the shaft 212S of the motor 212. Thereby, a groove, which is a region surrounded by the outer surface of the small disk 202 and end faces of the large disks 201A and 201B, is formed. The depth of the groove, i.e., the difference "T" in level between the small disk 202 and the large disks 201A and 201B, continuously varies depending upon the angular position of the small disk 202.

With reference to FIG. 4 and FIG. 5, when the motor 212 rotates the large disks 201A and 201B and the small disk 202 counterclockwise in FIG. 4, the viscosity of the liquid LQD is such that the liquid LQD adheres to the groove with a thickness corresponding to the continuously variable depth T. The liquid LQD may also adhere to the external circumference of the large disks 201A and 201B. Further, the liquid LQD may adhere over the groove, i.e., over the level of the outer surfaces of the large disks 201A and 201B, due to the surface (interfacial) tension of the liquid LQD. When the liquid LQD adheres above the level of the outer surfaces of the large disks 201A and 201B, the tip of the liquid LQD above the outer surfaces of the large disks 201A and 201B is scraped off by the first doctor blade 205. In addition, liquid adhered to the external circumference of the large disks 201A and 201B may also be scraped off by the first doctor blade 205.

Figure 6:
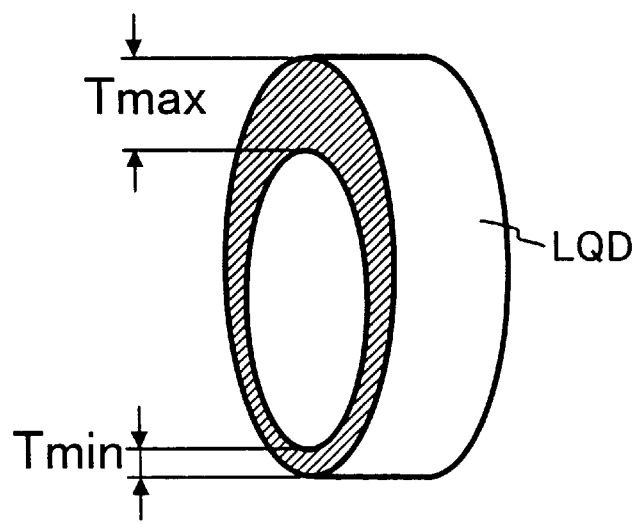
FIG. 6 is a perspective view illustrating a liquid formed on a disk of the concentration measuring device of FIG. 4.

FIG. 6 is a diagram illustrating that the shape of the adhered liquid LQD to the small disk 202 is substantially the same as the shape of the groove described above. Because the small disk 202 is eccentric relative to the large disks 201A and 201B, the thickness of the formed ring of liquid LQD varies from a minimum thickness Tmin to a maximum thickness Tmax depending upon the angular position of the small disk 202.

Figure 7:
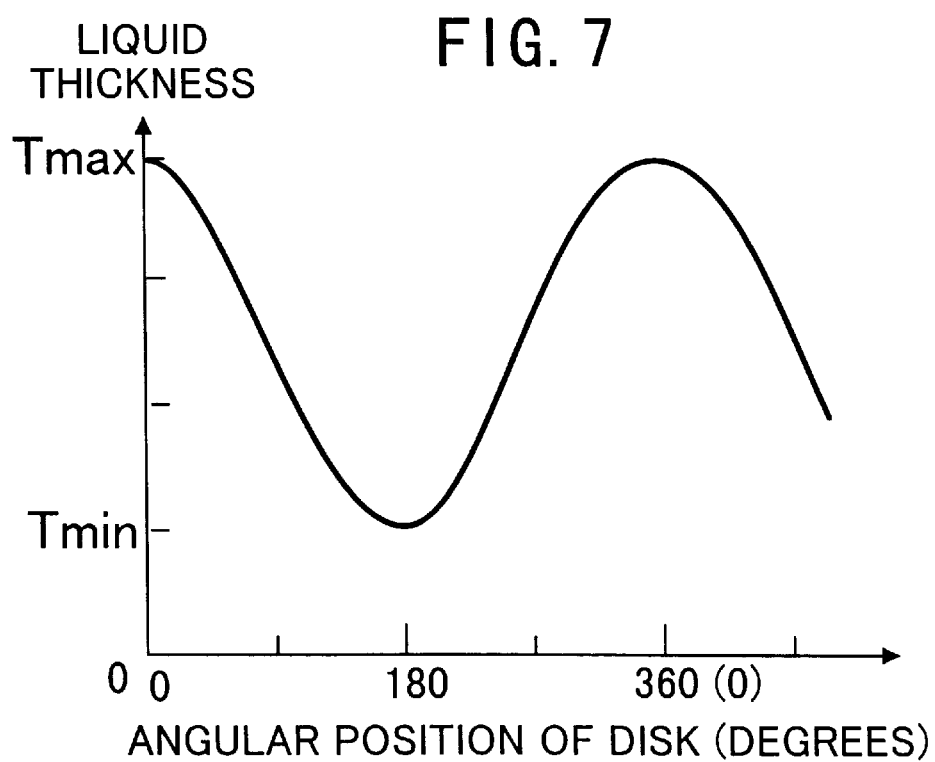
FIG. 7 is a graph illustrating a relationship between a thickness of the liquid and an angular position of the disk of the concentration measuring device of FIG. 4.

FIG. 7 is a graph illustrating a relationship between the liquid thickness and the angular position of the small disk 202. In this example, a relative angular position between the notch 203A and the small disk 202 is adjusted such that the notch sensor 211 detects the notch 203A of the notched disk 203 when the liquid LQD faces the optical sensor 207 at the maximum thickness Tmax. Accordingly, the thickness of the liquid LQD can be determined depending upon the angular position of the small disk 202 as illustrated in FIG. 7. For example, when the small disk 202 rotates 90 degrees, the thickness of the liquid LQD is about (Tmax+Tmin)/2, and when the small disk 202 rotates 180 degrees, the thickness of the liquid LQD is about Tmin. In addition, the notch sensor 211 and the notched disk 203 may be replaced with an angle sensor, such as an angular position encoder provided on the shaft 212S of the motor 212.

The minimum thickness Tmin and the maximum thickness Tmax of the liquid may be determined experimentally. As an example, for one type of liquid developer, a thickness of 40 micrometers for the minimum thickness Tmin, and a thickness of 160 micrometers for the maximum thickness Tmax may be used.

Referring back to FIG. 4, the optical sensor 207 is disposed at an angular position downstream from the first doctor blade 205 in the rotating direction of the small disk 202. The light emitting device 207A emits a light IL toward the surface of the small disk 202, so that the emitted light IL passes through the liquid layer having a thickness T. The emitted light IL is then reflected by the surface of the small disk 202, and the reflected light RL passes through the liquid layer again and impinges on the light receiving device 207B.

During the rotation of the small disk 202, the light emitting device 207A continuously emits the light IL, and the light receiving device 207B continuously receives the reflected light RL. Thus, the optical sensor 207 can output a signal according to the intensity of the light RL that twice passes through the liquid LQD of continuously variable thickness, i.e., from the minimum thickness Tmin to the maximum thickness Tmax.

When a solution or a dispersing liquid of the liquid LQD is optically transparent, and a substance, which is a solute or a dispersoid, is opaque or translucent, the intensity of the reflected light RL is inversely proportional to the substance concentration in the liquid LQD over a certain range of concentrations. The intensity of the reflected light RL is also inversely proportional to the thickness T of the liquid LQD. Accordingly, the optical sensor 207 continuously outputs a signal depending upon the substance concentration in the liquid LQD and the continuously variable thickness of the liquid LQD.

As the optical sensor 207, for example, a CTD sensor K03X-154, which includes a light emitting device and a light receiving device, produced by STANRAY ELECTRIC CO. may be used. Further, as the light emitting device 207A of the optical sensor 207, for example, a light emitting diode, a laser diode, a light bulb, an electroluminescence light, a cold-cathode tube, a fluorescent light, etc., may also be used. As the light receiving device 207B, for example, a photodiode, a phototransistor, a CCD image sensor, a CdS sensor, a photomultiplier tube, etc., may also be used.

The second doctor blade 206 contacts the outer surface of the small disk 202. Thereby, the liquid LQD, after measurement of substance concentration in the liquid by the optical sensor 207, is removed from the small disk 202. Then, the removed liquid LQD returns to the tank 242.

An output voltage or current of the optical sensor 207 may be observed by, for example, an oscilloscope, a voltmeter, an ammeter, etc., and recorded by a recorder such as an analyzing recorder AR4400 produced by YOKOGAWA ELECTRIC CO.

Figures 8, 9:
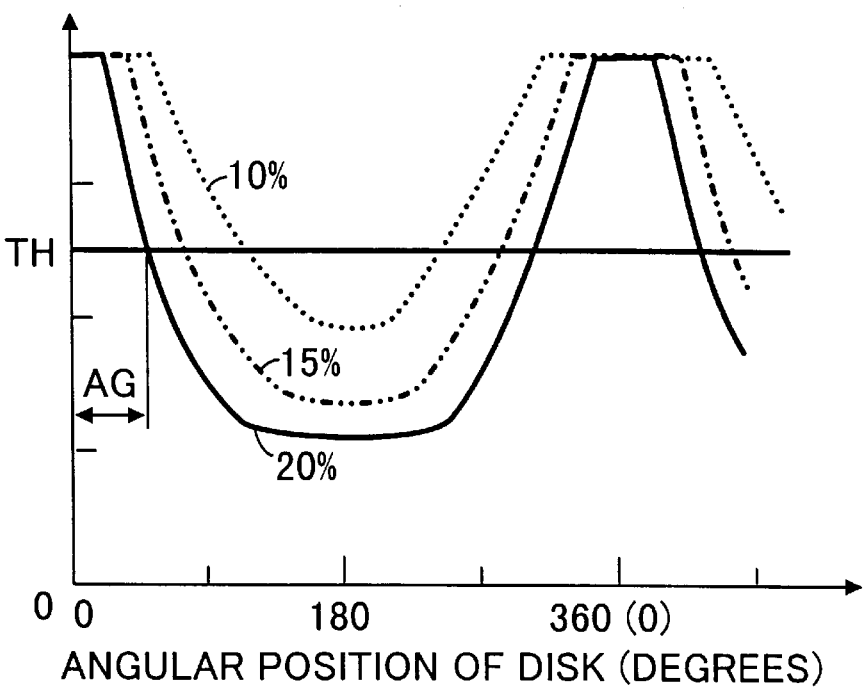
FIG. 8 is a graph illustrating a relationship between a sensor output voltage and an angular position of the disk of the concentration measuring device of FIG. 4.
FIG. 9 is a table illustrating a relationship between an angular position of the disk at which the sensor outputs a predetermined voltage and a substance concentration in a liquid.

FIG. 8 is a graph illustrating a relationship between the output voltage of the optical sensor 207 and the angular position of the small disk 202 of the concentration measuring device 200. In FIG. 8, the horizontal axis can be converted into a time (such as seconds) axis by dividing the angular position (degrees) of the small disk 202 by an angular velocity (degrees/second). A dotted curve denoted as. 10% illustrates an output for a liquid developer with a 10% toner concentration. Likewise, an alternate line and two dots curve denoted as 15% illustrates an output for a liquid developer with 15% toner concentration, and a solid line curve denoted as 20% illustrates an output for a liquid developer with a 20% toner concentration. As illustrated, the output voltage of the optical sensor 207 varies depending upon the toner concentration in the liquid developer and the angular position of the small disk 202, i.e., the thickness of the liquid LQD. The present invention capitalizes on these characteristics, i.e., the dependence on the substance concentration in the liquid and the thickness of the liquid, to measure a wide range of substance concentrations in a liquid with a single light emitting device and a single light receiving device.

The converter module 218 converts the output signal from the optical sensor 207 into a substance concentration in the liquid LQD. As an example, the converter module 218 may include an angular position detecting function that detects an angular position AG (FIG. 8) where the output voltage of the optical sensor 207 crosses a predetermined voltage TH (FIG. 8) and a conversion table. As illustrated in FIG. 8, the angular position AG varies depending upon the substance concentration in the liquid; therefore, the substance concentration can be determined.

FIG. 9 is a table in the converter module 218 illustrating a relationship between the angular position AG of the disk 202 at which the output voltage of the optical sensor 207 crosses the predetermined voltage TH and the substance concentration in the liquid. Because the angular position AG varies depending upon the substance concentration in the liquid LQD, the converter module 218 can convert an output voltage of the optical sensor 207 into an angular position AG of the disk 202, and then convert the angular position AG into a substance concentration in the liquid LQD. For example, when the angular position AG is AG1, the substance concentration in the liquid is determined as C1%, and the like.

The concentration measuring device 200 can be used for any of the liquid developing devices 140K, 140C, 140M and 140Y in the laser printer 100 of FIG. 3. When the concentration measuring device 200 is used in the laser printer 100, the output signal of the optical sensor 207 may be connected to the control module 103 (FIG. 3), and the control module 103 can perform the function of the converter module 218. For example, the conversion table of FIG. 9 may be stored in the flash memory 103F. The angular position detecting function that detects the angular position AG and converting function that converts the angular positiop AG into a substance concentration in the liquid are performed by the CPU 103C by executing a program.

Figure 10:
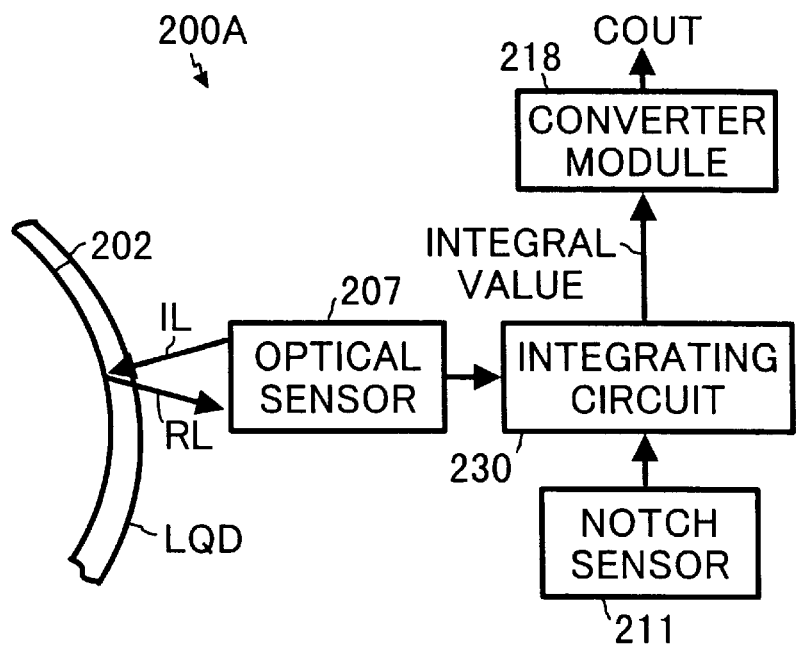
FIG. 10 is a block diagram illustrating a concentration measuring device having an integrating circuit.

As another example, the output voltage of the optical sensor 207 may be integrated. FIG. 10 is a block diagram illustrating a concentration measuring device 200A having an integrating circuit. In FIG. 10, the elements that are substantially the same as those in FIG. 4 and FIG. 5 are denoted by the same reference numerals. A description of the same elements in FIG. 10 as in FIG. 4 and FIG. 5 is not provided here to avoid redundancy. Referring to FIG. 10, the concentration measuring device 200A further includes an integrating circuit 230 that receives an input from the optical sensor 207 and an input from the notch sensor 211. When the integrating circuit 230 receives the input from the notch sensor 211, the integrating circuit 230 resets an output denoted as INTEGRAL VALUE to zero volts, and then continuously integrates the input signal from the optical sensor 207 and continuously outputs the integral value for the input signal until receiving the next input from the notch sensor 211.

Figure 11:
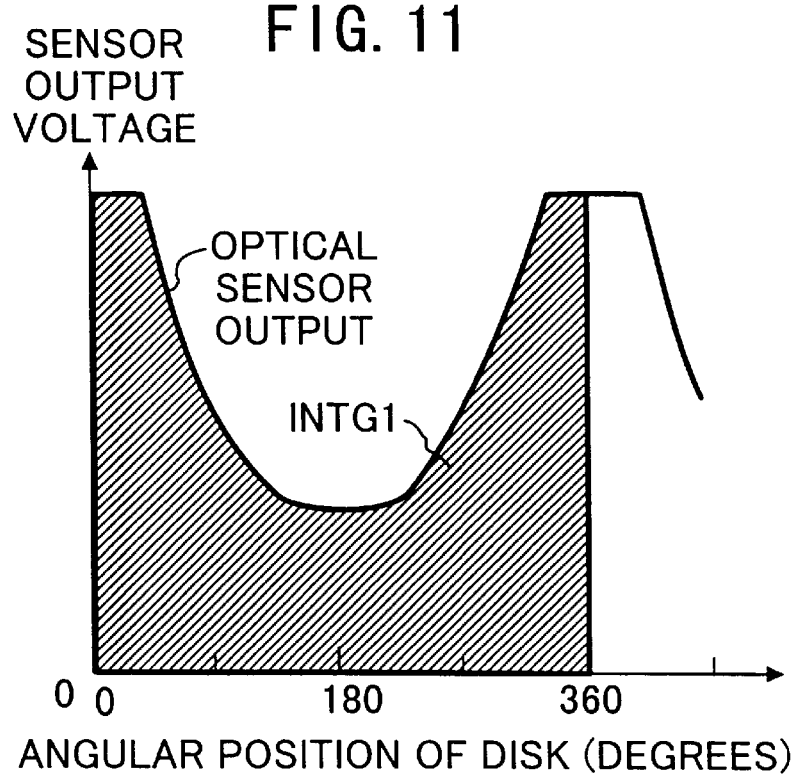
FIG. 11 is a graph illustrating the integration of a sensor output voltage.

FIG. 11 is a diagram for explaining the integration of the output voltage of the optical sensor 207. Referring to FIG. 11, when the optical sensor 207 outputs a voltage as a curve denoted as OPTICAL SENSOR OUTPUT, the integrating circuit 230 integrates the input voltage of the curve and outputs the integral value of the input voltage. The integral value is equivalent to the area enclosed by the input voltage curve, the vertical and horizontal axes, and a vertical line at an angular position of the small disk 202. Accordingly, immediately before the integrating circuit 230 receives the input from the notch sensor 211, the integrating circuit 230 outputs an integral value equivalent to the area shaded and denoted as INTG1 in FIG. 11.

Figure 12:
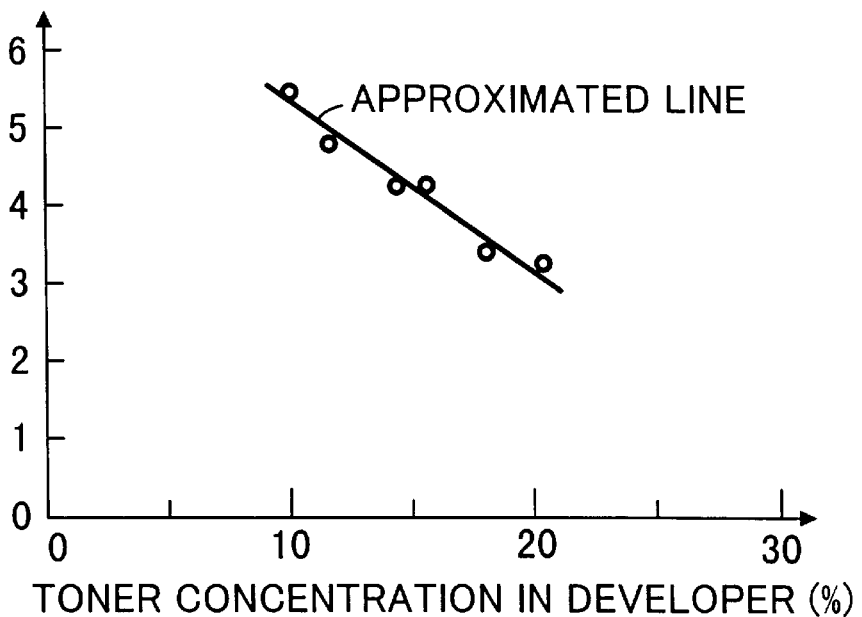
FIG. 12 is a graph illustrating a relationship between an integral value output from the concentration measuring device of FIG. 10 and a toner concentration in a liquid developer.

FIG. 12 is a graph illustrating a relationship between an output of the integral value and a toner concentration in a developer. Small circles illustrate experimentally obtained data according to the above-described integration method, and a line denoted as APPROXIMATED LINE is obtained by a correlation analysis. As illustrated in FIG. 12, the output of the integral value and the toner concentration in the developer are approximated by a linear function within a range from 10% to 20% toner concentration in the developer.

The integral value is then converted into a substance concentration of the liquid by the converting module 218. For example, the converting module 218 may have a conversion table provided with plural sets of an integral value and a substance concentration, and thereby the converting module 218 can convert an integral value into a substance concentration in a liquid. Thus, the concentration measuring device 200A can measure a relatively wide range of substance concentrations in a liquid while maintaining an approximately constant sensitivity.

Further, the integrating operation suppresses spike noises which may be included in the output signal of the optical sensor 207. Accordingly the integrating operation may result in a relatively more stable measurement.

When the concentration measuring device 200B is used in the laser printer 100 of FIG. 3, the integrating circuit 230 and the converting module 218 can be replaced with the control module 103 of FIG. 3. The output signal of the optical sensor 207 is connected to analog input terminals of the input device 103I of the control module 103, and thereby the analog input signal is converted into digital data. Then, the CPU 103C integrates the converted digital voltage, and obtains an integral value. Then, the CPU 103C converts the integral value into a substance concentration in the liquid, i.e., a toner concentration in the developer. The program code for the integrating operation and the converting operation of an integral value into a substance concentration, which is executed by the CPU 103C, may be stored in the flash memory 103F. Thus, the integrating circuit 211 and the converting module are replaced by the control module 103 of FIG. 3.

Figure 13:
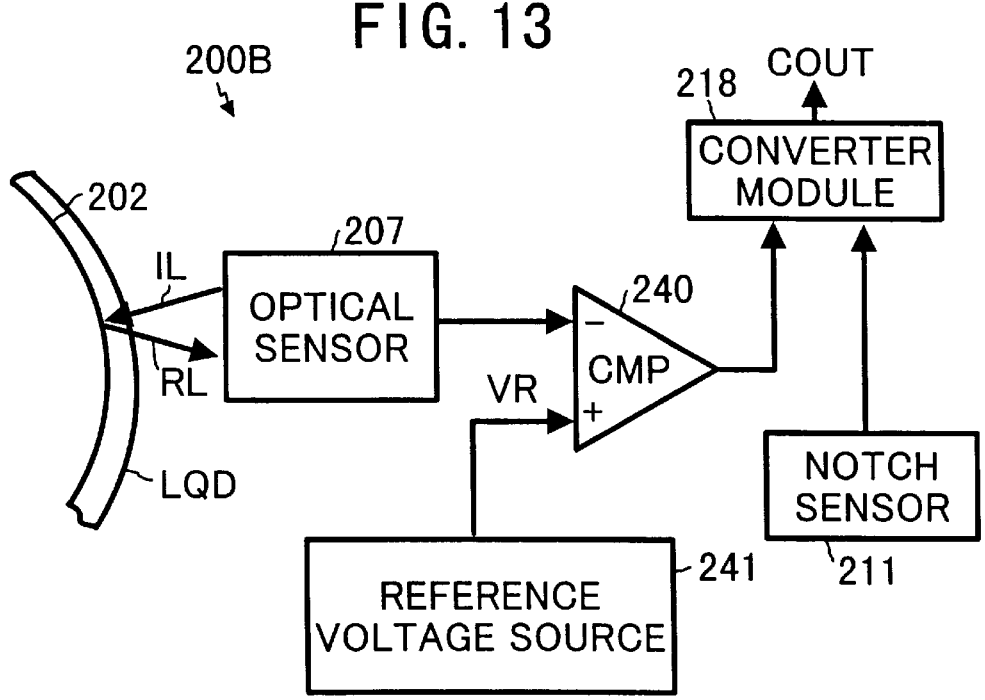
FIG. 13 is a block diagram illustrating a concentration measuring device having a voltage comparator.

FIG. 13 is a schematic diagram illustrating a concentration measuring device 200B having a voltage comparator. In FIG. 13, the elements that are substantially the same as those in FIG. 4 and FIG. 5 are denoted by the same reference numerals. Referring to FIG. 13, the concentration measuring device 200B further includes a reference voltage source 241 and a voltage comparator 240 denoted as CMP. The voltage comparator 240 receives an input from the optical sensor 207 and a reference voltage VR from the reference voltage source 241. When the voltage comparator 240 receives an input from the optical sensor 207 smaller than the reference voltage VR, the voltage comparator 240 outputs a positive voltage VS; otherwise, the voltage comparator 240 outputs zero volts. Accordingly, the pulse width of the output VS of the voltage comparator 240 varies depending upon the waveform input from the optical sensor 207.

Figure 14A:
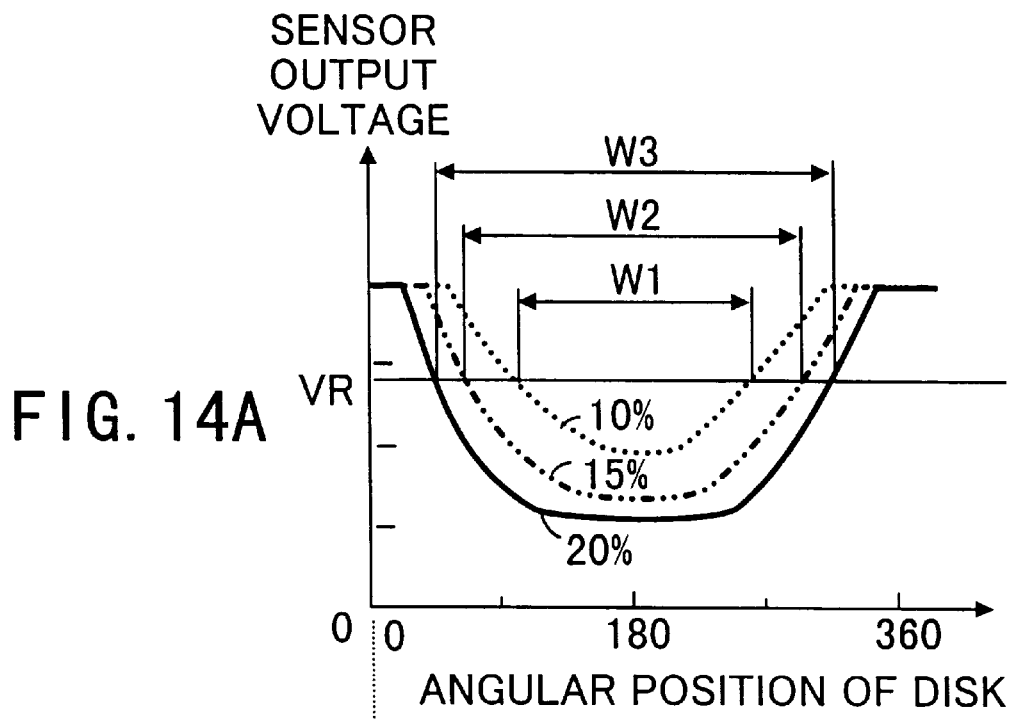
FIGS. 14A, 14B, 14C and 14D are diagrams for explaining the output of the voltage comparator of FIG. 13.
Figure 14B:
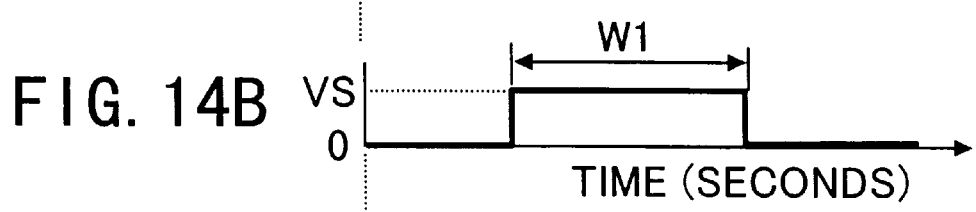
Figure 14C:
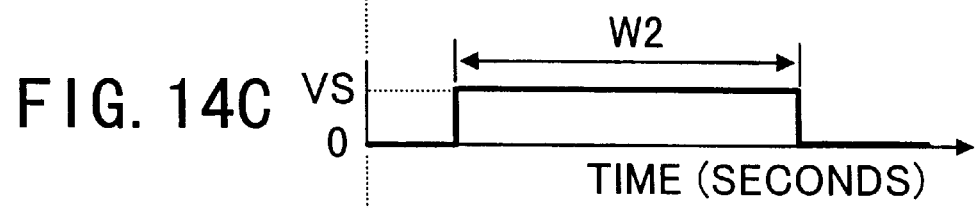
Figure 14D:
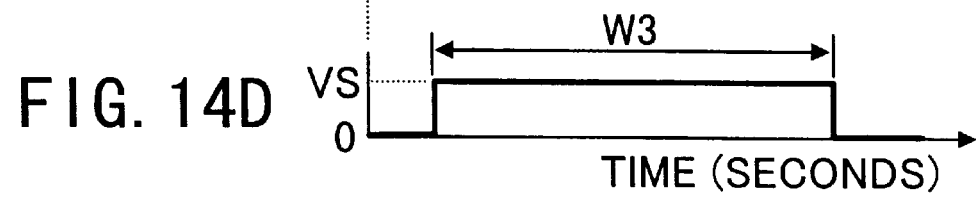

FIGS. 14A, 14B, 14C and 14D are diagrams for explaining the output signal of the voltage comparator 240. In FIG. 14A, each of the widths W1, W2 and W3 corresponds to a width of a waveform input from the optical sensor 207 below the reference voltage VR. In FIG. 14A, the horizontal axis can be converted into a time (e.g., seconds) axis by dividing the angular position (degrees) of the small disk 202 by an angular velocity (degrees/second). Accordingly, when the optical sensor 207 outputs a voltage for a developer with 10% concentration of toner, the voltage comparator 240 outputs a pulse of which width W1 as illustrated in FIG. 14B. Similarly, for a developer with 15% concentration of toner, the voltage comparator 240 outputs a pulse of width W2 as illustrated in FIG. 14C, and for a developer with 20% concentration of toner, the voltage comparator 240 outputs a pulse of width W3 as illustrated in FIG. 14D.

As described, the width of the pulse varies depending upon the substance concentration in the liquid, and consequently the converting module 218 can convert the width of the pulse into a substance concentration in the liquid.

When the concentration measuring device 200B is used in the laser printer 100 of FIG. 3, the output of the optical sensor 207 may be connected to an analog input terminal of the input device 103I of the control module 103 of FIG. 3. Therefore, the analog input voltage is converted into digital data by the input device 103I. Then, the CPU 103C compares the converted digital data with the reference voltage VR, which may be stored in the flash memory 103F, and then obtains a period where the converted digital data is smaller than the reference voltage VR. Then, the CPU 103C converts the period into a substance concentration in a liquid, i.e., a toner concentration in the developer.

Figure 15:
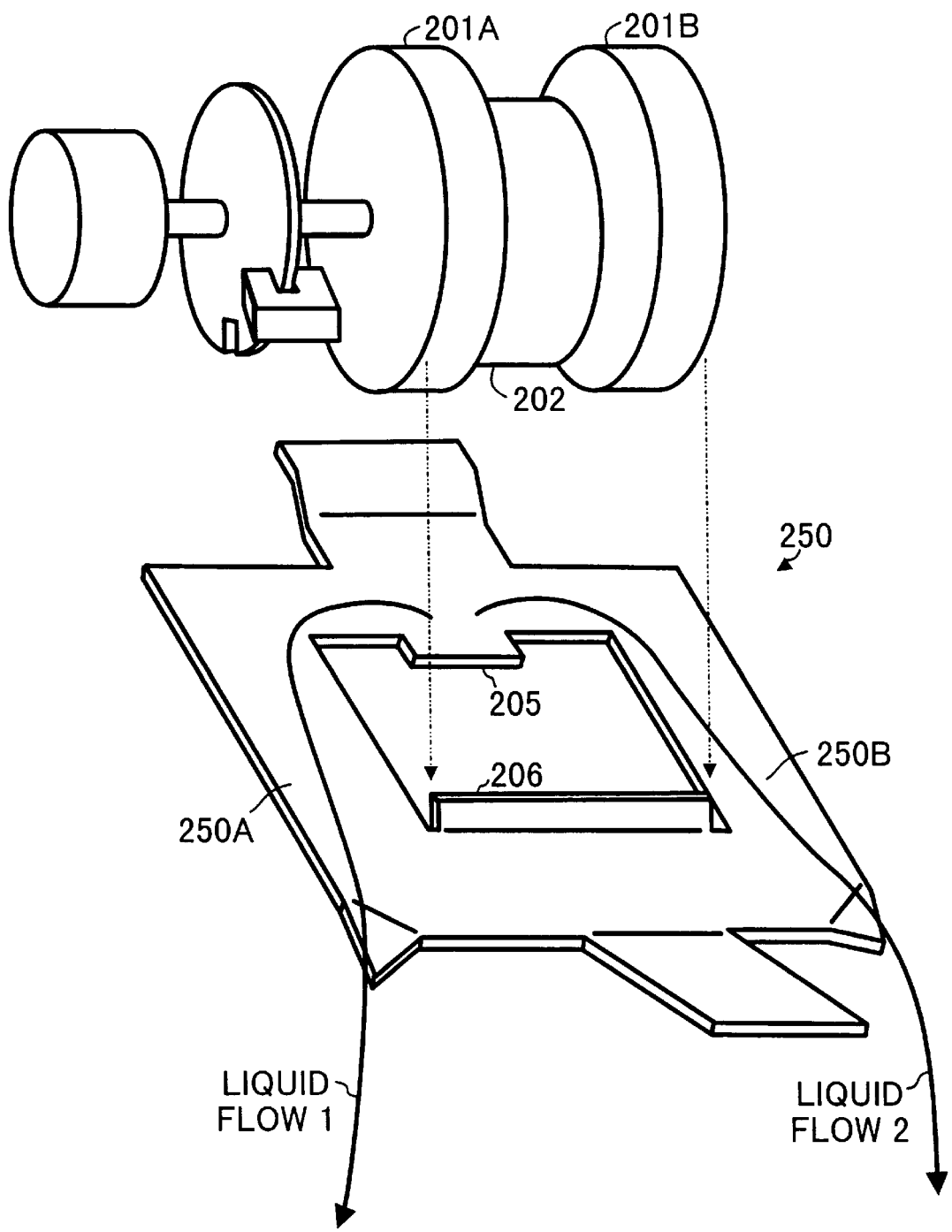
FIG. 15 is a schematic view illustrating a blade and liquid path module.

FIG. 15 is a schematic view illustrating a structure of a blade and liquid path module 250. In FIG. 15, the elements that are substantially the same as those in FIG. 4 and FIG. 5 are denoted by the same reference numerals, and a description of those elements is not provided. The blade and liquid path module 250 includes a first blade 205, a second blade 206, and liquid paths 250A and 250B. The blade and liquid path module 250 is formed as a single piece, which may be made of a sheet metal, a molded plastic, a molded rubber, etc. Therefore, relative dimensions such as, a dimension between the first blade 205 and the second blade 206 may be precisely maintained, and production costs of the blades 205 and 206 may be reduced. Liquid removed from the surface of the small disk 202 by the second blade 206 flows on the liquid paths 250A and 250B such as along the arrows denoted as LIQUID FLOW 1 and LIQUID FLOW 2. The liquid paths 250A and 250B guide the liquid removed from the surface of the small disk 202 to fall into a different place apart from a place where the liquid adheres to the small disk 202.

Figure 16:
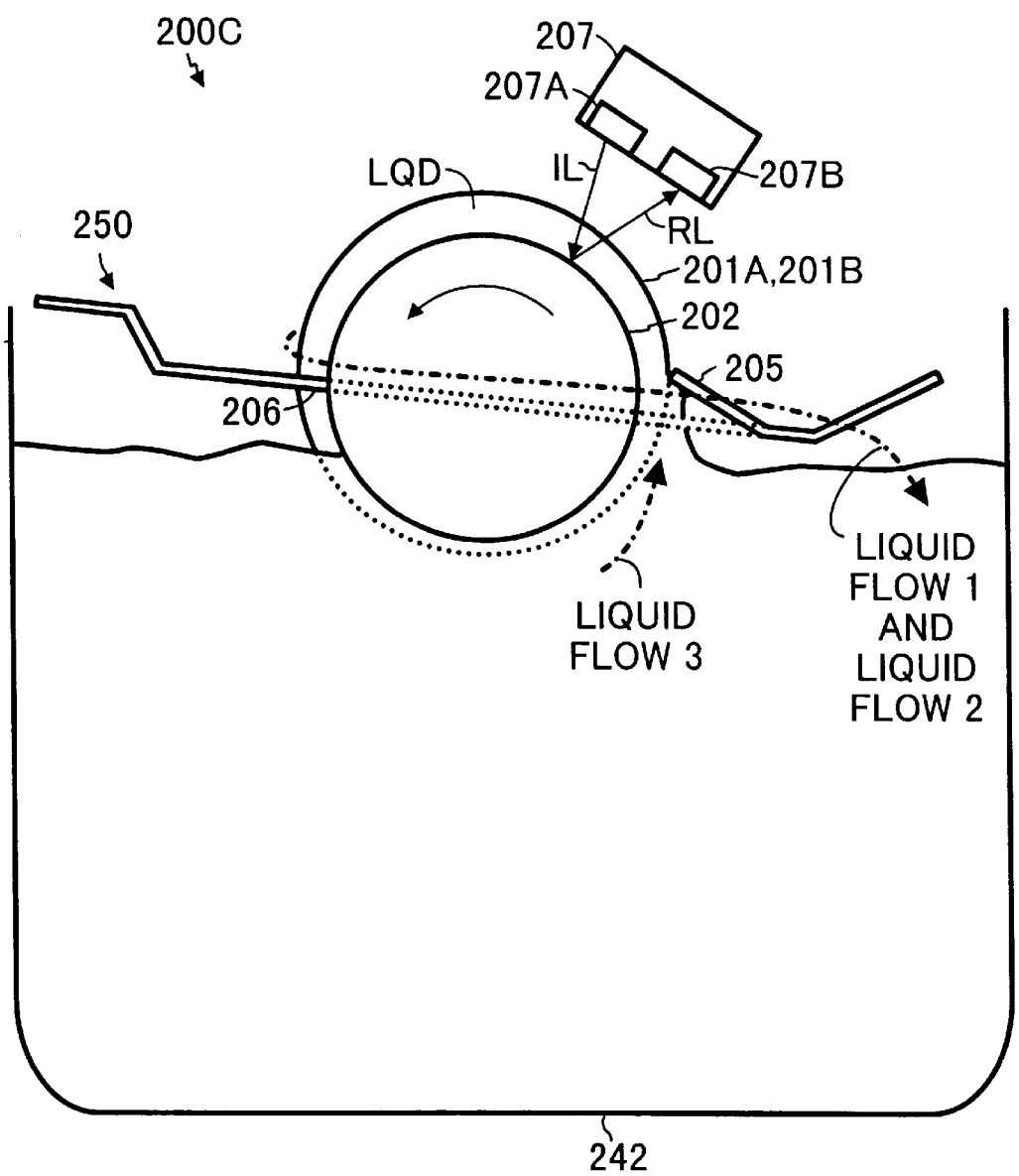
FIG. 16 is a schematic sectional view illustrating a structure of a concentration measuring device having the blade and liquid path module of FIG. 15.

FIG. 16 is a schematic sectional view illustrating a structure of a concentration measuring device 200C having the blade and liquid path module 250 of FIG. 15. With reference to FIG. 16, liquid removed from the surface of the small disk 202 by the second blade 206 flows on the liquid paths 250A and 250B such as the arrows denoted as LIQUID FLOW 1 AND LIQUID FLOW 2. A liquid flow that is going to adhere to the small disk 202 is illustrated as an arrow denoted as LIQUID FLOW 3. That is, the liquid paths 250A and 250B transport the removed liquid to a place different from where the liquid is applied to the small disk 202. In other words, the same portion of the liquid does not always adhere to the small disk 202. Therefore even if the substance concentration in the liquid rapidly changes, the capability of measuring the concentration is not deteriorated.

Figure 17:
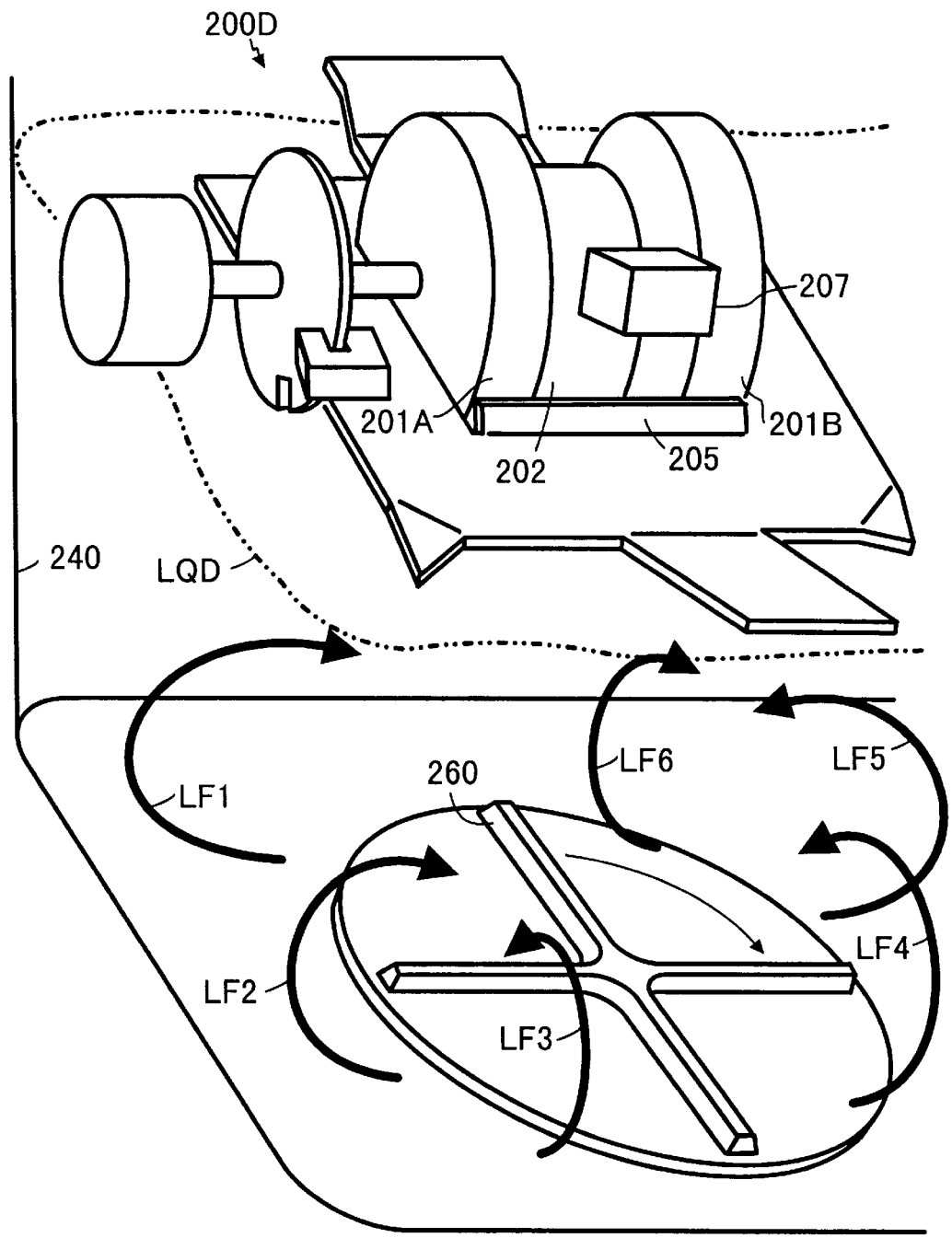
FIG. 17 is a schematic sectional view illustrating a structure of a concentration measuring device having a liquid agitator.

FIG. 17 is a schematic sectional view illustrating a structure of a concentration measuring device 200D having a liquid agitator. The concentration measuring device 200D further includes a vaned wheel 260 as a liquid agitator at the bottom of the tank 240. The vaned wheel 260 causes liquid flows illustrated as arrows LF1 to LF6, and consequently the capability of measuring a changing substance concentration in liquid LQD is further increased. In addition a vibrating device that vibrates the tank 24b may also be used as a liquid agitator.

Figure 18A:
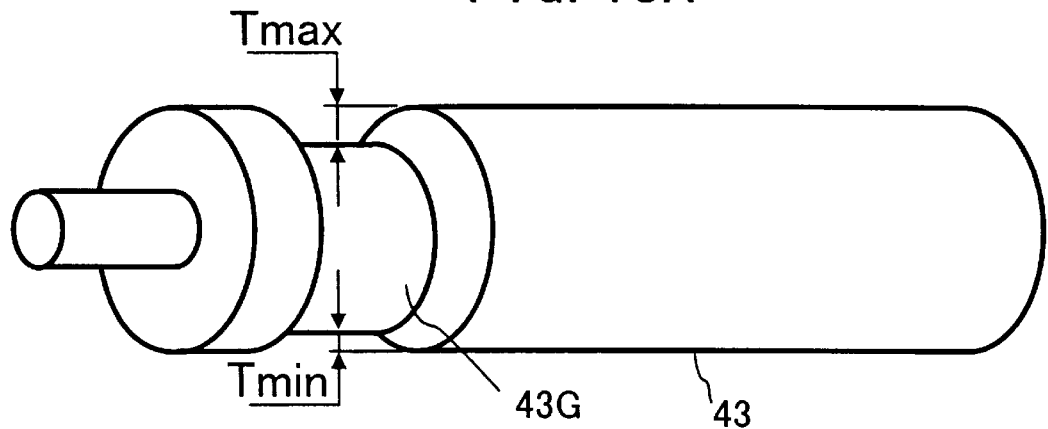
FIG. 18A is a schematic view illustrating a developer supply roller having an eccentric groove.

When the measuring device of the present invention is used in an image forming apparatus such as the laser printer 100 of FIG. 3, a device for forming a continuously variable thickness of a liquid may be formed at an end of one of a developer supply roller, a developer coating roller, or a developing roller. FIG. 18A is a schematic view illustrating a developer supply roller 43 having an eccentric groove 43G. The groove 43G has a smaller diameter in comparison with the external diameter of the developer supply roller 43. In addition, the groove 43G is formed to be eccentric to the external diameter such that the depth of the groove 43G varies from Tmax at most to Tmin at least. The groove 43G can contain a liquid developer at a thickness depending upon the angular position of the groove 43G, and thereby a sensor such as the optical sensor 207 of FIG. 4 can output a signal dependent upon the continuously variable thickness of the liquid developer.

Figure 18B:
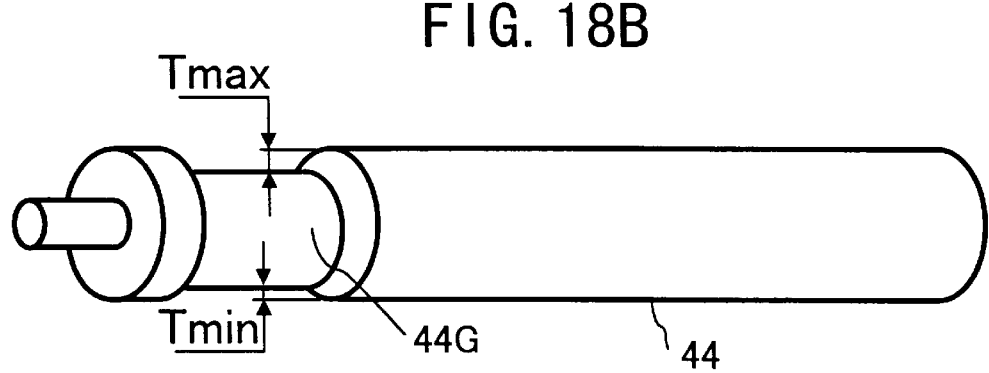
FIG. 18B is a schematic view illustrating a developer coating roller having an eccentric groove.

FIG. 18B is a schematic view illustrating a developer coating roller 44 having an eccentric groove 44G. The groove 44G has a smaller diameter in comparison with the external diameter of the developer supply roller 44. In addition, the groove 44G is also formed to be eccentric to the external diameter such that the groove depth varies from Tmax at most to Tmin at least. The groove 44G can contain a liquid developer of a thickness depending upon the angular position of the groove 44G, and thereby a sensor such as the optical sensor 207 of FIG. 4 can output a signal dependent upon the continuously variable thickness of the liquid developer.

Figure 19:
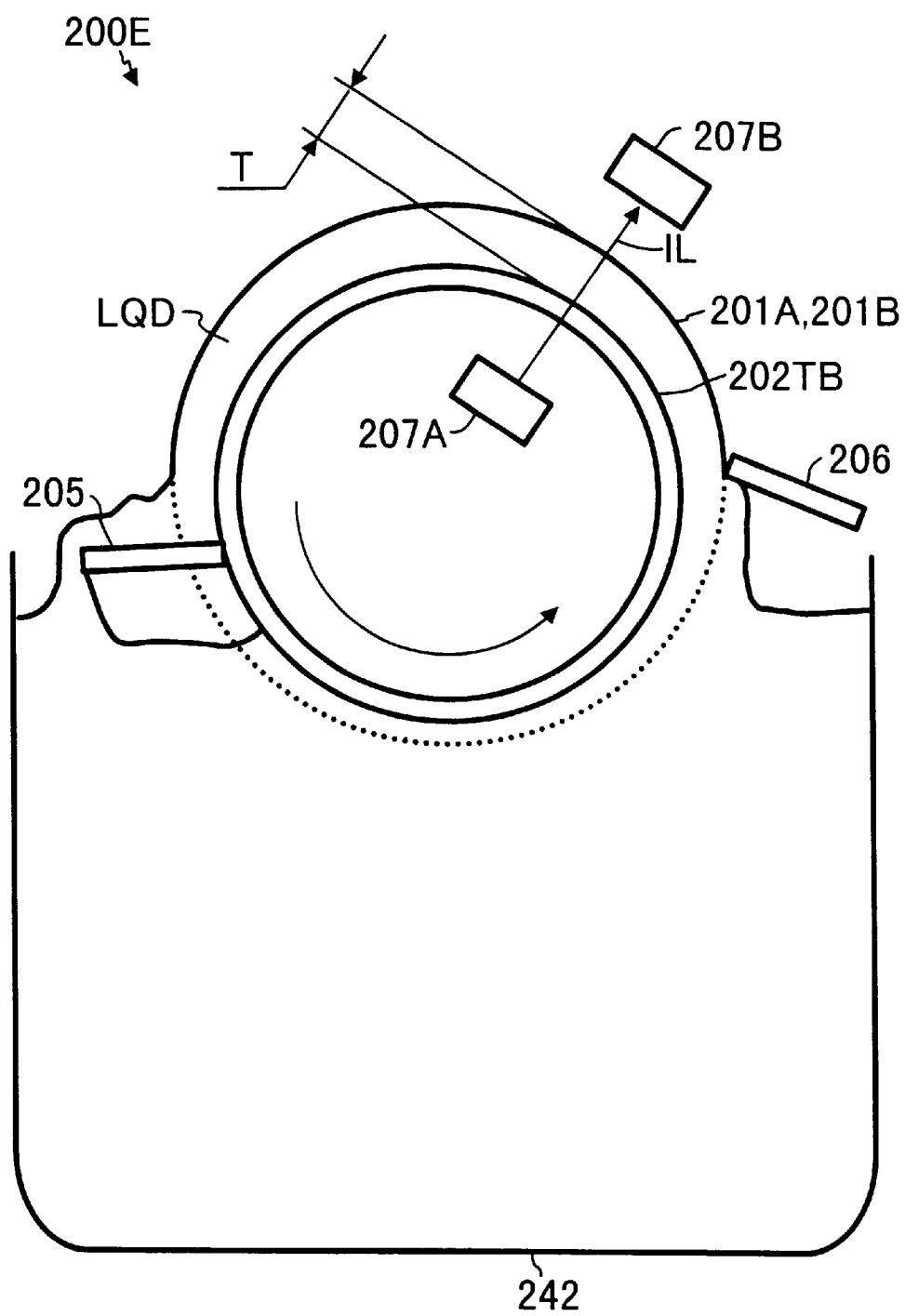
FIG. 19 is a schematic sectional view illustrating a structure of a concentration measuring device having an optically transparent tube.

FIG. 19 is a schematic sectional view illustrating a structure of a concentration measuring device 200E having an optically transparent tube. In FIG. 19, the elements that are substantially the same as those in FIG. 4 and FIG. 5 are denoted by the same reference numerals, and a description of those elements is not provided. Referring to FIG. 19; the large disks 201A and 201B have substantially identical external diameters, and an optically transparent tube 202TB has a smaller external diameter than that of the large disks 201A and 201B. The optically transparent tube 202TB is sandwiched by the large disks 201A and 201B, and is eccentric relative to the large disks 201A and 201B. Thereby, the difference "T" in level between small disk 202 and the large disks 201A and 201B varies depending upon the angular position of the optically transparent tube 202TB. The large disks 201A and 201B, and the optically transparent tube 202TB may be formed as a single piece with a transparent plastic, for example, by an injection molding method.

A light emitting device 207A is disposed inside the optically transparent tube 202TB, and a light receiving device 207B is disposed outside the optically transparent tube 202TB to receive the light emitted and passed through the optically transparent tube 202TB and the liquid LQD.

The relationship between the liquid thickness and the angular position of the optically transparent tube 202TB is substantially the same as that of the concentration measuring device of FIG. 4 as illustrated in the graph of FIG. 7. In addition, because the light emitted by the light emitting device 207A penetrates only once through the liquid layer LQD, the liquid thickness T may be thicker than that of the device of FIG. 4. For example, a minimum thickness may be 80 25 micrometers, and a maximum thickness may be 320 micrometers.

Figure 20:
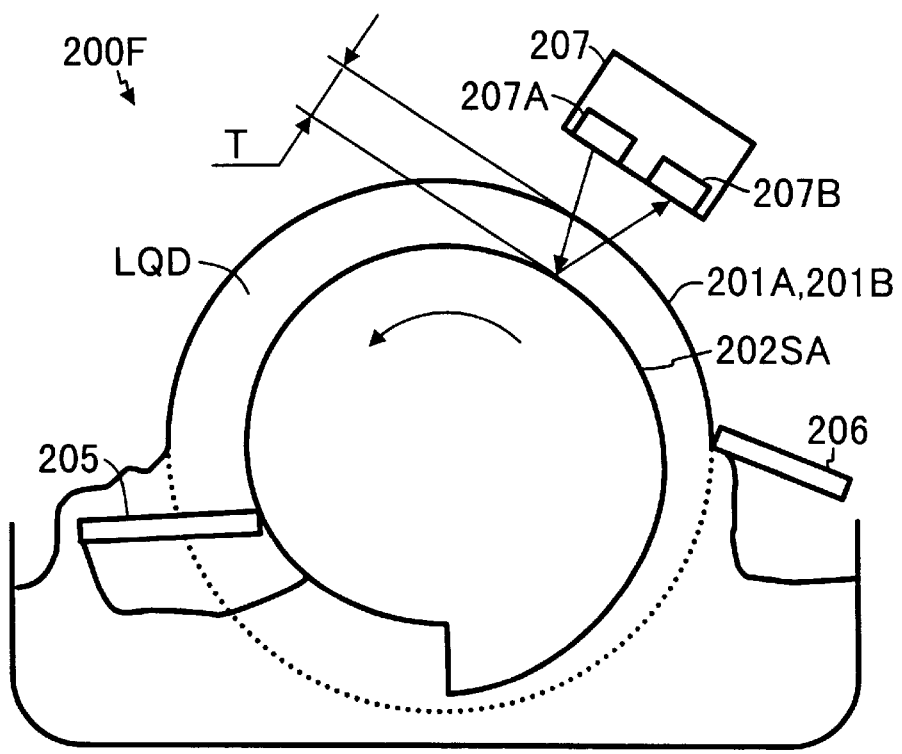
FIG. 20 is a schematic sectional view illustrating a structure of a concentration measuring device having a spiral disk.

FIG. 20 is a schematic sectional view illustrating an example of a concentration measuring device 200F having a spiral disk. In FIG. 20, the elements that are substantially the same as those in FIG. 4 and FIG. 5 are denoted by the same reference numerals, and a description of those elements is not provided. Referring to FIG. 20, the large disks 201A and 201B have the same external diameters, and a spiral disk 202SA has a smaller external circumscribing diameter than the large disks 201A and 201B. The spiral disk 202SA is sandwiched by the large disks 201A and 201B. A difference "T" in level between the spiral disk 202SA and the large disks 201A and 201B varies depending upon an angular position of the disks.

Figure 21:
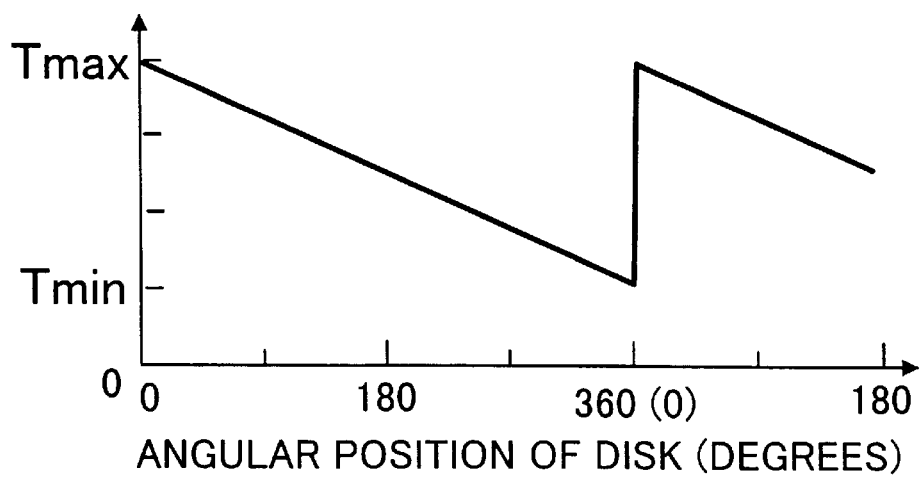
FIG. 21 is a graph illustrating a relationship between a liquid thickness and an angular position of the spiral disk of FIG. 20.

FIG. 21 is a graph illustrating a relationship between liquid thickness and angular position of the spiral disk 202SA. As illustrated, when the spiral disk 202SA is used instead of the circular disk such as the disk 202 of FIG. 4, the rate of change of the liquid thickness becomes smaller. Accordingly, the measurement of the substance concentration in the liquid may be more precisely performed.

Figure 22:
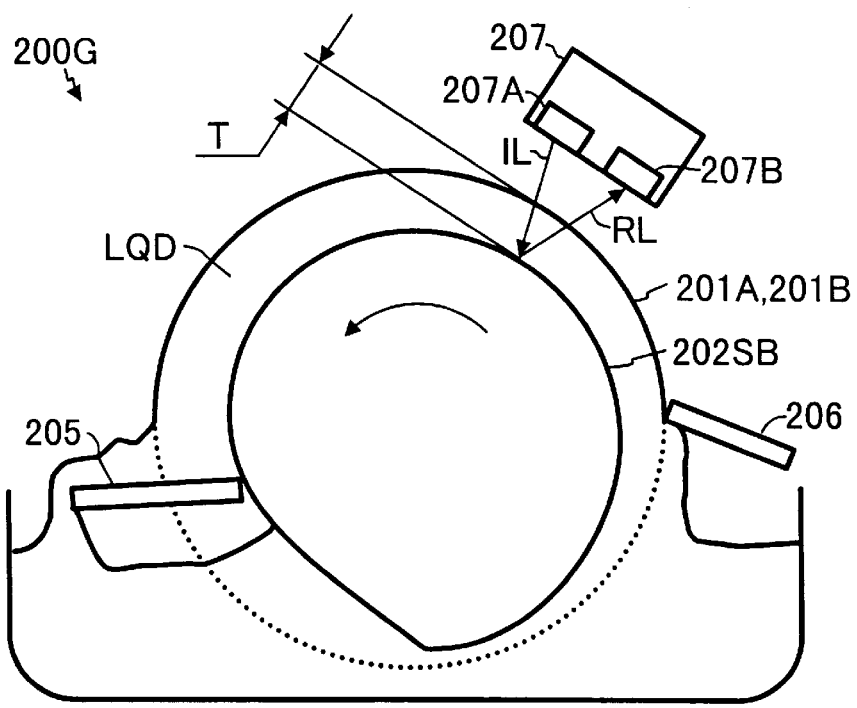
FIG. 22 is a schematic sectional view illustrating a structure of a concentration measuring device having another type of spiral disk.

FIG. 22 is a schematic sectional view illustrating a structure of a concentration measuring device 200G having another type of spiral disk 202SB. All elements other than the spiral disk 202SB are substantially the same as those in FIG. 20. The spiral disk 202SB does not have a sharp difference in level in comparison with the spiral disk 202SA of FIG. 20. Therefore, the liquid LQD on the spiral disk 202SB may be easily removed by the second doctor blade 205. In addition, the spiral disk 202SB may also be manufactured by a numerically controlled cylindrical grinding machine and not only by a lathe.

Figure 23:
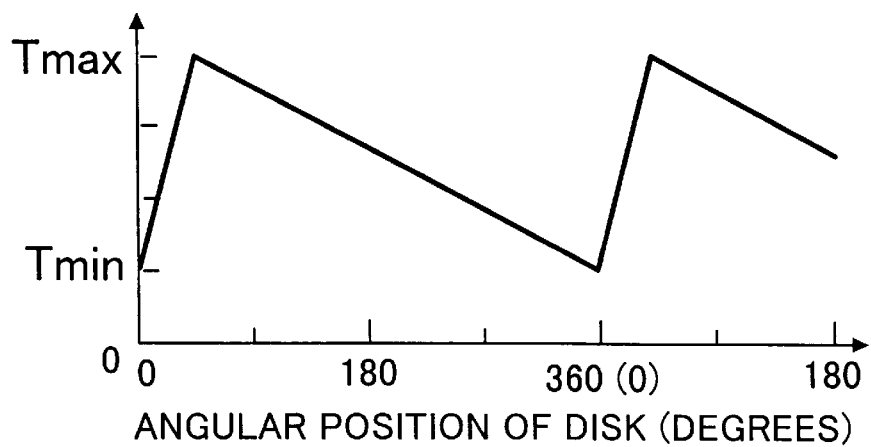
FIG. 23 is a graph illustrating a relationship between a liquid thickness and an angular position of the spiral disk of FIG. 22.

FIG. 23 is a graph illustrating a relationship between a thickness of the liquid and an angular position of the spiral disk 202SB.

Figure 24:
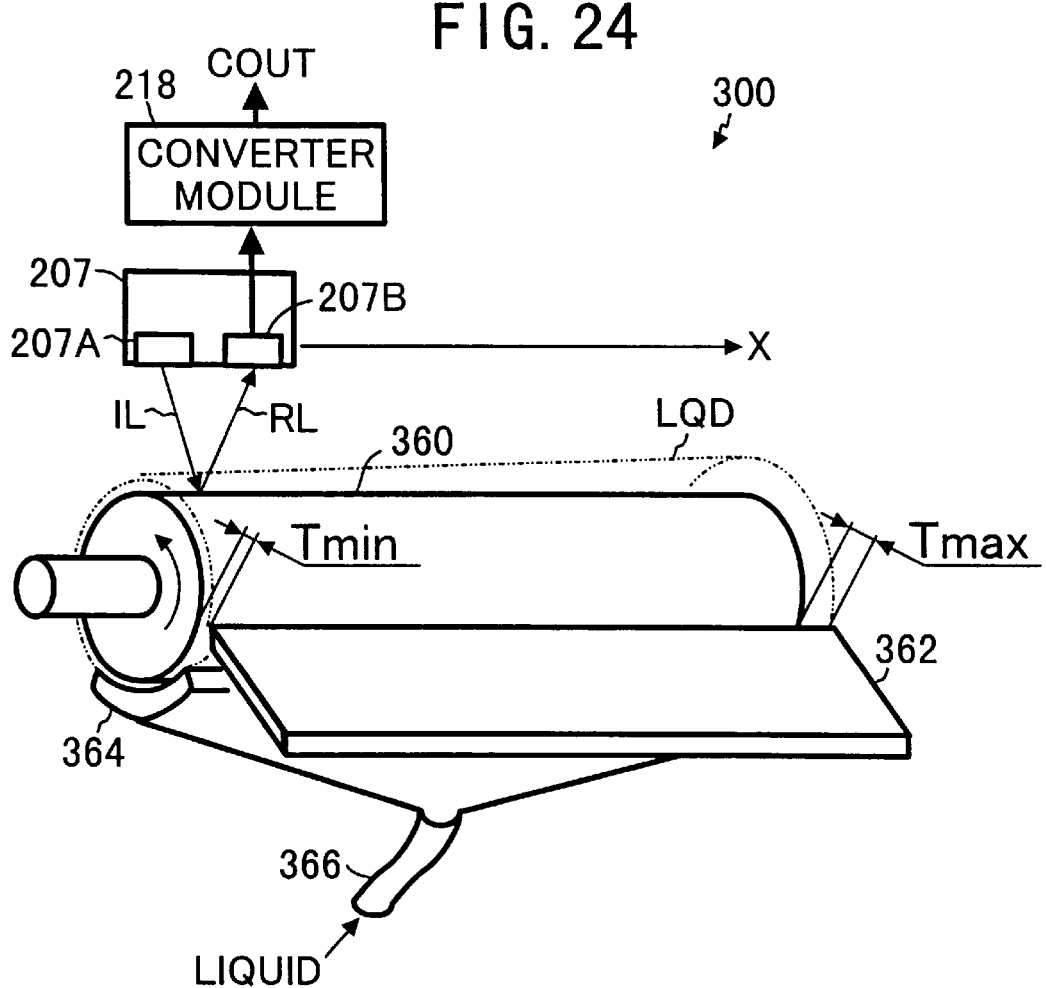
FIG. 24 is a schematic view illustrating a structure of a concentration measuring device as another example configured according to the present invention.

FIG. 24 is a schematic view illustrating a structure of a concentration measuring device 300 as another example configured according to the present invention. In FIG. 24, elements that are substantially the same as those in FIG. 4 and FIG. 5 are denoted by the same reference numerals. Referring to FIG. 24, the concentration measuring device 300 includes an optical sensor 207, a roller 360, a metering blade 362, a liquid applicator 364, and a liquid pipe 366 connecting to the liquid applicator 364.

The roller 360 rotates and its surface reflects light. The liquid applicator 364 applies a liquid in which substance concentration is to be measured to the rotating roller 360 and is supplied with the liquid via the liquid pipe 366. The metering blade 362 is disposed at a distance Tmin from the circumference of the roller 360 at one end and a distance Tmax from the circumference of the roller 360 at the other end of the roller 360 at a position downstream from the liquid applicator 364. Thereby, the roller 360 carries a liquid layer LQD of variable thickness from Tmin to Tmax along the axis of the roller 360.

The optical sensor 207 includes a light emitting device 207A and a light receiving device 207B, both opposing the outer surface of the roller 360. The optical sensor 207 travels from one end to the other end of the roller 360 along an arrow denoted as X. During the travel, the light emitting device 207A emits light IL, and the light receiving device 207B receives light RL reflected on the surface of the roller 360. Both the incident light IL and the reflected light RL penetrate the liquid layer LQD. Accordingly, the intensity of the light received by the light receiving device 207B is decreased in proportion with the substance concentration in the liquid and the thickness of the liquid LQD.

Figure 25:
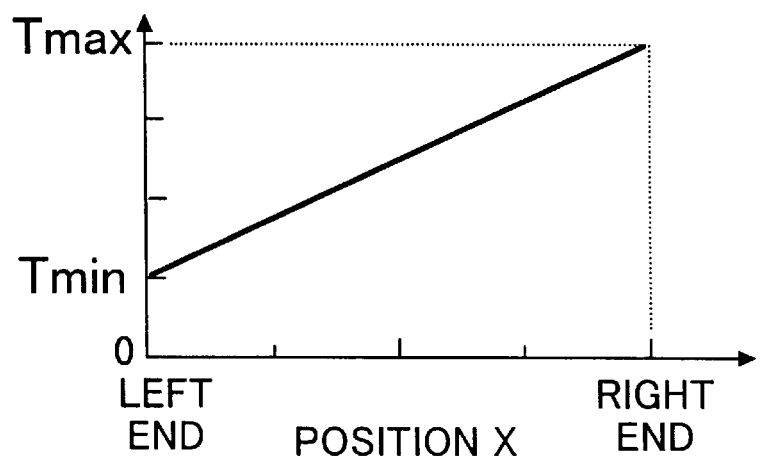
FIG. 25 is a graph illustrating a relationship between a liquid thickness and a position of an optical sensor of FIG. 24.

FIG. 25 is a graph illustrating a relationship between a thickness of the liquid and a position X of the optical sensor 207. Accordingly, the light receiving device 207B can output a signal dependent upon the continuously variable thickness of the liquid.

In addition, when the concentration measuring device 300 is used in an image forming apparatus such as the laser printer 100 of FIG. 3, the liquid applicator 364 and the connecting liquid pipe 366 may be omitted by dipping the lower portion of the roller 360 in the liquid developer 146Y in a developer tank 142Y, for example.

Figure 26:
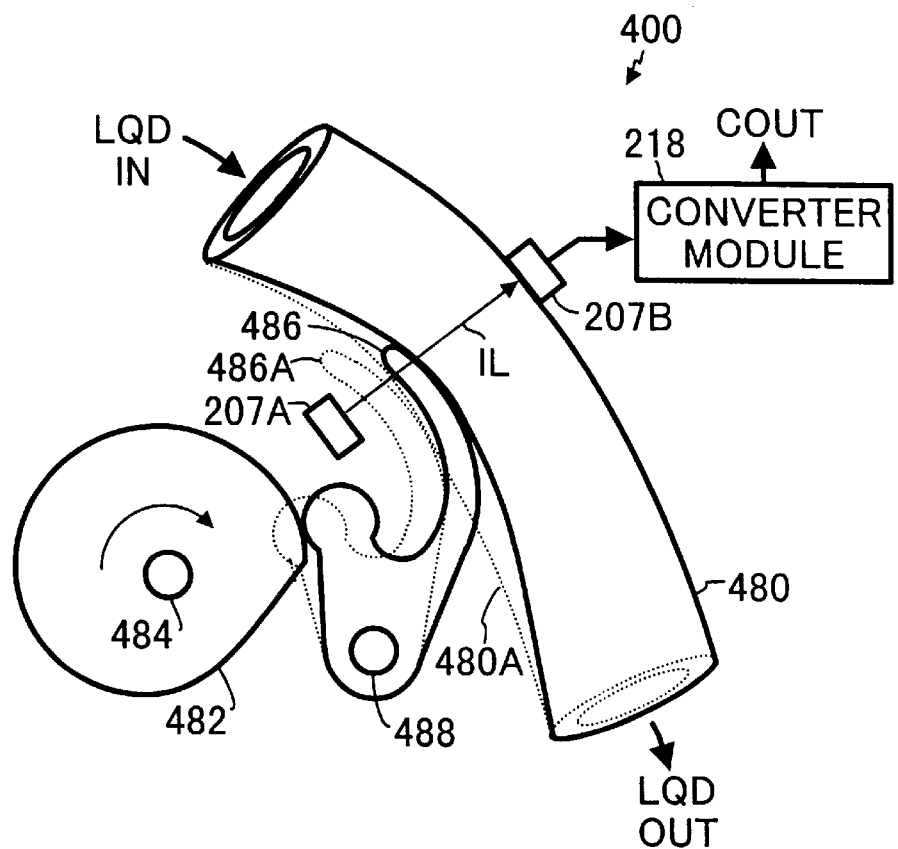
FIG. 26 is a schematic view illustrating a structure of a concentration measuring device as a further example configured according to the present invention.

FIG. 26 is a schematic view illustrating a structure of a concentration measuring device 400 as a further example configured according to the present invention. In FIG. 26, the elements that are substantially the same as those in FIG. 4 and FIG. 5 are denoted by the same reference numerals. Referring to FIG. 24, the concentration measuring device 400 includes a flexible channel 480, a cam 482 mounted on a rotating shaft 484, a cam follower 486 pivoted on a shaft 488, a light emitting device 207A, and a light receiving device 207B. The flexible channel 480 and the cam follower 486 are optically transparent. The light emitting device 207A is disposed at one side of the flexible channel 480 and the light receiving device 207B is disposed at the other side of the flexible channel 480. The light emitting device 207A emits a light IL, and the light receiving device 207B receives the light.

The flexible channel 480 conducts a liquid, in which substance concentration is to be measured, as illustrated by arrows LQD IN and LQD OUT. The cam 482 rocks the cam follower 486 between a position illustrated by solid line 486 and a position illustrated by dotted line 486A. The cam follower 486 compresses the flexible channel 480 to change the thickness of the channel 480 between a position illustrated by solid line 480 and a position illustrated by dotted line 480A. As a result, the thickness of the liquid where the light IL penetrates varies from a minimum of Tmin to a maximum of Tmax.

Figure 27:
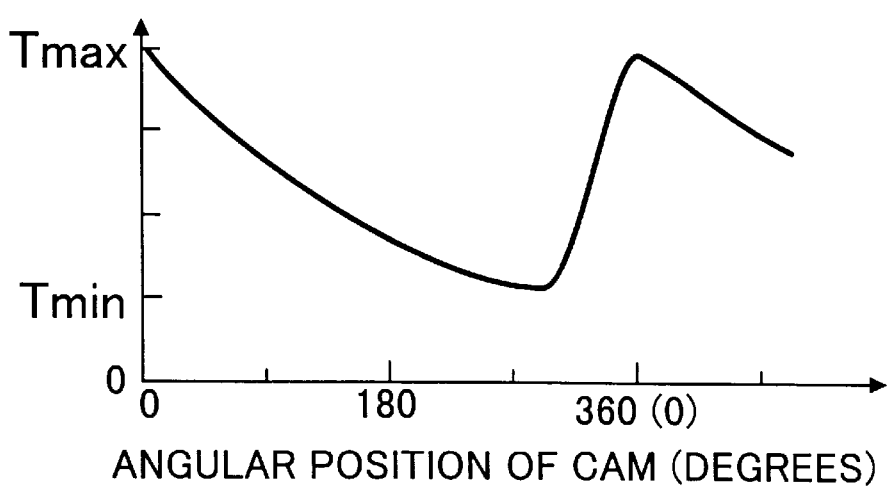
FIG. 27 is a graph illustrating a relationship between a liquid thickness and an angular position of a cam of FIG. 26.

FIG. 27 is a graph illustrating a relationship between a thickness of the liquid and an angular position of the cam 482. When the liquid is semitransparent, the intensity of the light received by the light receiving device 207B varies depending upon the thickness of the liquid and the substance concentration in the liquid.

Thus, the light receiving device 207B can output a signal according to a continuously variable thickness of the liquid.

In addition, when the concentration measuring device 400 is used in an image forming apparatus such as the laser printer 100 of FIG. 3, an optically transparent flexible pipe that is already provided such as a transporting pipe that connects a preservation tank to the developing device 140Y can be used as the flexible channel.

Described above is a novel method and a device for measuring a substance concentration in a solution. This method can measure a relatively wide range of substance concentrations in a liquid using a single light emitting device and a single light receiving device.

Numerous modifications and variations of the present invention are possible in light of the above teachings. For example, features described for certain embodiments may be combined with other embodiments described herein. It is therefore to be understood that within the scope of the appended claims, the invention may be practiced otherwise than as specifically described herein.

What is claimed as new and is desired to be secured by Letters Patent of the United States is:

1. A method for measuring a substance concentration in a liquid, comprising:

forming a continuously variable thickness of the liquid on a rotating roller;

emitting light towards the continuously variable thickness of the liquid such that a portion of the emitted light passes through said continuously variable thickness of the liquid;

generating an electrical signal according to the portion of the light that has passed through the formed continuously variable thickness of the liquid; and determining the substance concentration in the liquid based on the generated electrical signal.

2. The method according to claim 1, wherein said determining step comprises:

integrating the generated electrical signal to produce an integral value; and determining the substance concentration based on the integral value.

3. The method according to claim 1, wherein said determining step comprises:

measuring a period of time between two predetermined output values of the generated electrical signal; and determining the substance concentration in the liquid based on the measured period of time.

4. The method according to claim 1, wherein the forming step comprises:

forming the continuously variable thickness of the liquid between two rotating concentric first disks having substantially identical first diameters and on a second disk having a second diameter, smaller than the first diameter, said second disk being eccentrically sandwiched by the two first disks.

5. The method according to claim 1, wherein the forming step comprises:

forming the continuously variable thickness of the liquid on the rotating roller by a metering doctor blade disposed at a first predetermined distance from an end of the roller and at a second predetermined distance from an other end of the roller.

6. The method according to claim 1, wherein the forming step comprises:

forming the continuously variable thickness of the liquid by flowing the liquid through an optically transparent flexible channel; and varying the thickness of said optically transparent flexible channel.

7. An apparatus for measuring a substance concentration in a liquid comprising:

a liquid layer forming device configured to form a continuously variable thickness of the liquid on a rotating roller;

a light emitting device configured to emit a light such that a portion of the emitted light passes through the continuously variable thickness of the liquid;

a light receiving device configured to generate an electrical signal according to the portion of the emitted light that has penetrated the continuously variable thickness of the liquid; and a determining device configured to determine the substance concentration in the liquid based on the generated electrical signal.

8. The apparatus according to claim 7, wherein said determining device comprises:

an integrating device configured to integrate the generated electrical signal, said determining device configured to determine the substance concentration in the liquid based on an integral value.

9. The apparatus according to claim 7, wherein said determining device comprises:

a measuring device configured to measure a period of time between two predetermined output values of the generated electrical signal, said determining device configured to determine the substance concentration in the liquid based on the measured period of time.

10. The apparatus according to claim 7, wherein the liquid layer forming device comprises:

two rotating concentric disks having substantially identical first diameters; and a second disk having a second diameter smaller than the first diameters and being eccentrically sandwiched by the two rotating concentric disks.

11. The apparatus according to claim 10, wherein the liquid layer forming device further comprises:

a first doctor blade configured to scrape off a tip of the continuously variable thickness of the liquid on the second disk and an excess liquid layer on the first disks; and a second doctor blade configured to scrape off the continuously variable thickness of the liquid on the second disk.

12. The apparatus according to claim 10, wherein the liquid layer forming device further comprises:

a single piece module having a first doctor blade configured to scrape off a tip of the continuously variable thickness of the liquid above the first disks;

a second doctor blade configured to remove the continuously variable thickness of the liquid on the second disk; and a liquid transporting path that transports the scraped off liquid.

13. The apparatus according to claim 7, wherein the liquid layer forming device comprises:

a metering doctor blade disposed at a first predetermined distance from an end of the roller and at a predetermined distance from an end of the roller and at a second predetermined distance from an other end of the roller.

14. The apparatus according to claim 7, wherein the liquid layer forming device comprises:

an optically transparent flexible channel configured to have a thickness; and an actuating device configured to vary the thickness of the optically transparent flexible channel at a portion where the light emitted by the light emitting device passes through the optically transparent flexible channel.

15. The apparatus according to claim 7, wherein the liquid layer forming device comprises:

two rotating concentric disks configured to have substantially identical first diameters; and a spiral disk configured to have a circumscribed circle diameter smaller than the first diameters and sandwiched by the two rotating concentric disks.

16. The apparatus according to claim 7, wherein the liquid layer forming device comprises:

two rotating concentric disks having substantially identical first diameters; and an optically transparent tube having an external diameter smaller than the first diameters and being eccentrically sandwiched by the two rotating concentric disks, wherein one of the light emitting device and the light receiving device is disposed inside the optically transparent tube and the other is disposed outside the optically transparent tube.

17. The apparatus according to claim 7, further comprising:

a removing device configured to remove the liquid from the liquid layer forming device thereby configured to generate a removed liquid; and a liquid transporting path configured to transport the removed liquid to a different place from a place where the liquid is applied to the liquid layer forming device.

18. The apparatus according to claim 7, further comprising:
an agitating device configured to agitate the liquid before the liquid is applied to the liquid layer forming device.

19. A device for measuring a substance concentration in a liquid, comprising:
means for forming a continuously variable thickness of the liquid on a rotating roller;
means for emitting a light such that a portion of the light passes through the formed continuously variable thickness of the liquid;
means for generating an electrical signal according to the portion of the light that has passed through the continuously variable thickness of the liquid; and
means for determining the substance concentration in the liquid based on the generated electrical signal.

20. The image forming apparatus according to either claim 19 or 7, wherein the substance concentration comprises:
a toner concentration.

21. An image forming apparatus comprising:
an image bearing device configured to bear an image;
a developing device configured to develop the image on the image bearing device by a liquid developer having a developer concentration;
a liquid developer layer forming device configured to form a continuously variable thickness of the liquid developer on a rotating roller;
a light emitting device configured to emit a light such that a portion of the light passes through the continuously variable thickness of the liquid developer;
a light receiving device configured to generate an electrical signal according to the portion of the light that has passed through the formed continuously variable thickness of the liquid developer; and
a control device configured to determine the developer concentration in the liquid developer based on the generated electrical signal and control the developer concentration in the liquid developer according to the determined developer concentration in the liquid developer.

22. The image forming apparatus according to claim 21, wherein the liquid developer layer forming device is formed at an end of one of a developing roller, a developer supplying roller, and a developer applying roller.

23. An image forming apparatus comprising:
means for bearing an image;
means for developing the image on the image bearing means by a liquid developer having a developer concentration;
means for forming a continuously variable thickness of the liquid developer on a rotating roller;
means for emitting a light such that a portion of the light passes through the continuously variable thickness of the liquid developer;
means for generating an electrical signal according to the portion of the light that has passed through the continuously variable thickness of the liquid developer; and
means for determining a developer concentration in the liquid developer based on the generated electrical signal.

24. The image forming apparatus according to claim 23, wherein the forming means comprises:
two rotating concentric disks having substantially identical first diameters; and
a second disk having a second diameter smaller than the first diameters and being eccentrically sandwiched by the two rotating concentric disks.

25. The image forming apparatus according to claim 23, wherein the forming means comprises:
two rotating concentric disks having substantially identical first diameters; and
a spiral disk having a circumscribed circle diameter smaller than the first diameters and being sandwiched by the two rotating concentric disks.

26. The image forming apparatus according to claim 23, further comprising:
means for controlling the developer concentration in the liquid developer according to the determined developer concentration in the liquid developer.

27. The image forming apparatus according to either claim 21 or 23, wherein the developer concentration comprises:
a toner concentration.

28. A method for measuring a substance concentration in a liquid, comprising:
forming a continuously variable thickness of the liquid;
emitting light towards the continuously variable thickness of the liquid such that a portion of the emitted light passes through said continuously variable thickness of the liquid;
generating an electrical signal according to the portion of the light that has passed through the formed continuously variable thickness of the liquid; and
determining the substance concentration in the liquid based on the generated electrical signal, wherein said determining step comprises:
integrating the generated electrical signal to produce an integral value; and
determining the substance concentration based on the integral value.

29. A method for measuring a substance concentration in a liquid, comprising:
forming a continuously variable thickness of the liquid;
emitting light towards the continuously variable thickness of the liquid such that a portion of the emitted light passes through said continuously variable thickness of the liquid;
generating an electrical signal according to the portion of the light that has passed through the formed continuously variable thickness of the liquid; and
determining the substance concentration in the liquid based on the generated electrical signal, wherein said determining step comprises:
measuring a period of time between two predetermined output values of the generated electrical signal; and
determining the substance concentration in the liquid based on the measured period of time.

30. A method for measuring a substance concentration in a liquid, comprising:
forming a continuously variable thickness of the liquid;
emitting light towards the continuously variable thickness of the liquid such that a portion of the emitted light passes through said continuously variable thickness of the liquid;

generating an electrical signal according to the portion of the light that has passed through the formed continuously variable thickness of the liquid; and determining the substance concentration in the liquid based on the generated electrical signal, wherein the forming step comprises:

forming the continuously variable thickness of the liquid between two rotating concentric first disks having substantially identical first diameters and on a second disk having a second diameter, smaller than the first diameter, said second disk being eccentrically sandwiched by the two first disks.

31. A method for measuring a substance concentration in a liquid, comprising:

forming a continuously variable thickness of the liquid;

emitting light towards the continuously variable thickness of the liquid such that a portion of the emitted light passes through said continuously variable thickness of the liquid;

generating an electrical signal according to the portion of the light that has passed through the formed continuously variable thickness of the liquid; and determining the substance concentration in the liquid based on the generated electrical signal; wherein the forming step comprises:

forming the continuously variable thickness of the liquid on a rotating roller by a metering doctor blade disposed at a first predetermined distance from an end of the roller and at a second predetermined distance from an other end of the roller.

32. An apparatus for measuring a substance concentration in a liquid comprising:

a liquid layer forming device configured to form a continuously variable thickness of the liquid;

a light emitting device configured to emit a light such that a portion of the emitted light passes through the continuously variable thickness of the liquid;

a light receiving device configured to generate an electrical signal according to the portion of the emitted light that has penetrated the continuously variable thickness of the liquid; and a determining device configured to determine the substance concentration in the liquid based on the generated electrical signal, wherein said determining device comprises:

an integrating device configured to integrate the generated electrical signal, said determining device configured to determine the substance concentration in the liquid based on an integral value.

33. An apparatus for measuring a substance concentration in a liquid comprising:

a liquid layer forming device configured to form a continuously variable thickness of the liquid;

a light emitting device configured to emit a light such that a portion of the emitted light passes through the continuously variable thickness of the liquid;

a light receiving device configured to generate an electrical signal according to the portion of the emitted light that has penetrated the continuously variable thickness of the liquid; and a determining device configured to determine the substance concentration in the liquid based on the generated electrical signal, wherein said determining device comprises:

a measuring device configured to measure a period of time between two predetermined output values of the generated electrical signal, said determining device configured to determine the substance concentration in the liquid based on the measured period of time.

34. An apparatus for measuring a substance concentration in a liquid comprising:

a liquid layer forming device configured to form a continuously variable thickness of the liquid;

a light emitting device configured to emit a light such that a portion of the emitted light passes through the continuously variable thickness of the liquid;

a light receiving device configured to generate an electrical signal according to the portion of the emitted light that has penetrated the continuously variable thickness of the liquid; and a determining device configured to determine the substance concentration in the liquid based on the generated electrical signal, wherein the liquid layer forming device comprises:

two rotating concentric disks having substantially identical first diameters; and a second disk having a second diameter smaller than the first diameters and being eccentrically sandwiched by the two rotating concentric disks.

35. The apparatus according to claim 34, wherein the liquid layer forming device further comprises:

a first doctor blade configured to scrape off a tip of the continuously variable thickness of the liquid on the second disk and an excess liquid layer on the first disks; and a second doctor blade configured to scrape off the continuously variable thickness of the liquid on the second disk.

36. The apparatus according to claim 34, wherein the liquid layer forming device further comprises:

a single piece module having a first doctor blade configured to scrape off a tip of the continuously variable thickness of the liquid above the first disks;

a second doctor blade configured to remove the continuously variable thickness of the liquid on the second disk; and a liquid transporting path that transports the scraped off liquid.

37. An apparatus for measuring a substance concentration in a liquid comprising:

a liquid layer forming device configured to form a continuously variable thickness of the liquid;

a light emitting device configured to emit a light such that a portion of the emitted light passes through the continuously variable thickness of the liquid;

a light receiving device configured to generate an electrical signal according to the portion of the emitted light that has penetrated the continuously variable thickness of the liquid; and a determining device configured to determine the substance concentration in the liquid based on the generated electrical signal, wherein the liquid layer forming device comprises:

a rotating roller; and a metering doctor blade disposed at a first predetermined distance from an end of the roller and at a second predetermined distance from an other end of the roller.

38. An apparatus for measuring a substance concentration in a liquid comprising:

a liquid layer forming device configured to form a continuously variable thickness of the liquid;

a light emitting device configured to emit a light such that a portion of the emitted light passes through the continuously variable thickness of the liquid;

a light receiving device configured to generate an electrical signal according to the portion of the emitted light that has penetrated the continuously variable thickness of the liquid; and a determining device configured to determine the substance concentration in the liquid based on the generated electrical signal, wherein the liquid layer forming device comprises:

two rotating concentric disks having substantially identical first diameters; and a spiral disk having a circumscribed circle diameter smaller than the first diameters and being sandwiched by the two rotating concentric disks.

39. An apparatus for measuring a substance concentration in a liquid comprising:

a liquid layer forming device configured to form a continuously variable thickness of the liquid;

a light emitting device configured to emit a light such that a portion of the emitted light passes through the continuously variable thickness of the liquid;

a light receiving device configured to generate an electrical signal according to the portion of the emitted light that has penetrated the continuously variable thickness of the liquid; and a determining device configured to determine the substance concentration in the liquid based on the generated electrical signal, wherein the liquid layer forming device comprises:

two rotating concentric disks having substantially identical first diameters; and an optically transparent tube having an external diameter smaller than the first diameters and being eccentrically sandwiched by the two rotating concentric disks, wherein one of the light emitting device and the light receiving device is disposed inside the optically transparent tube and the other is disposed outside the optically transparent tube.

40. An image forming apparatus comprising:

means for bearing an image;

means for developing the image on the image bearing means by a liquid developer having a developer concentration;

means for forming a continuously variable thickness of the liquid developer;

means for emitting a light such that a portion of the light passes through the continuously variable thickness of the liquid developer;

means for generating an electrical signal according to the portion of the light that has passed through the continuously variable thickness of the liquid developer; and means for determining a developer concentration in the liquid developer based on the generated electrical signal, wherein the forming means comprises:

two rotating concentric disks having substantially identical first diameters; and a second disk having a second diameter smaller than the first diameters and being eccentrically sandwiched by the two rotating concentric disks.

41. An image forming apparatus comprising:

means for bearing an image;

means for developing the image on the image bearing means by a liquid developer having a developer concentration;

means for forming a continuously variable thickness of the liquid developer;

means for emitting a light such that a portion of the light passes through the continuously variable thickness of the liquid developer;

means for generating an electrical signal according to the portion of the light that has passed through the continuously variable thickness of the liquid developer; and means for determining a developer concentration in the liquid developer based on the generated electrical signal, wherein the forming means comprises:

two rotating concentric disks having substantially identical first diameters; and a spiral disk having a circumscribed circle diameter smaller than the first diameters and being sandwiched by the two rotating concentric disks.

42. A method for measuring a substance concentration in a liquid, comprising:

forming a continuously variable thickness of the liquid;

emitting light towards the continuously variable thickness of the liquid such that a portion of the emitted light passes through said continuously variable thickness of the liquid twice by reflection;

generating an electrical signal according to the portion of the light that has passed through the formed continuously variable thickness of the liquid; and determining substance concentration in the liquid based on the generated electrical signal.

* * * * *